US009080185B2

(12) United States Patent
Liao et al.

(10) Patent No.: US 9,080,185 B2
(45) Date of Patent: Jul. 14, 2015

(54) RECOMBINANT FLAVIVIRAL CONSTRUCTS AND USES THEREOF

(75) Inventors: Ching-Len Liao, Taipei County (TW); Jia-Teh Liao, Taipei (TW)

(73) Assignee: NATIONAL DEFENSIVE MEDICAL CENTER, Taipei (TW)

( * ) Notice: Subject to any disclaimer, the term of this patent is extended or adjusted under 35 U.S.C. 154(b) by 181 days.

(21) Appl. No.: 13/825,049

(22) PCT Filed: Sep. 20, 2011

(86) PCT No.: PCT/US2011/052379

§ 371 (c)(1), (2), (4) Date: Jun. 10, 2013

(87) PCT Pub. No.: WO2012/040218

PCT Pub. Date: Mar. 29, 2012

(65) Prior Publication Data

US 2013/0243809 A1 Sep. 19, 2013

Related U.S. Application Data

(60) Provisional application No. 61/384,720, filed on Sep. 21, 2010.

(51) Int. Cl.

| | |
|---|---|
| ***C12N 15/86*** | (2006.01) |
| ***A61K 39/12*** | (2006.01) |
| *A61K 39/00* | (2006.01) |

(52) U.S. Cl.

CPC ................ *C12N 15/86* (2013.01); *A61K 39/12* (2013.01); *A61K 2039/5254* (2013.01); *A61K 2039/5256* (2013.01); *C07K 2319/40* (2013.01); *C07K 2319/50* (2013.01); *C12N 2770/24122* (2013.01); *C12N 2770/24134* (2013.01); *C12N 2770/24143* (2013.01); *C12N 2770/32322* (2013.01); *C12N 2770/32334* (2013.01)

(58) Field of Classification Search

None

See application file for complete search history.

(56) References Cited

U.S. PATENT DOCUMENTS

2010/0184832 A1* 7/2010 Pugachev et al. ........... 514/44 R

FOREIGN PATENT DOCUMENTS

WO WO 2008/100464 A1 * 8/2008

* cited by examiner

*Primary Examiner* — Stacy B Chen

(74) *Attorney, Agent, or Firm* — Muncy, Geissler, Olds & Lowe, P.C.

(57) ABSTRACT

A recombinant viral construct for expressing an exogenous polypeptide in a cell and uses thereof are provided. The recombinant viral constructs are derived from Japanese encephalitis virus (JEV). The recombinant viral constructs encodes a fusion protein, which includes an exogenous (i.e., non-JEV) polypeptide and a JEV non-structural protein 1 (JEV NS1) or a segment thereof. Particularly, the exogenous polypeptide is inserted into the carboxyl-terminus of the JEV NS1, and the production of the recombinant fusion protein does not affect viral replication. Upon infection a cell with such recombinant viral constructs, JEV particles comprising limited multiplicative virions (LMV) may be produced. Each LMV comprises the as-described JEV replicon. The JEV particles are useful in eliciting an immune response to the exogenous polypeptide in a host and thereby confer the host with protective immunization against the exogenous polypeptide.

20 Claims, 15 Drawing Sheets

J-R2A-NS1-343SP70

[Ruc | NS1 | NS2A | 2B | NS3 | 4A | 4B | NS5]
CMVp

-DE T gal YPTFGEHKQEKDLEY asra T LV
343                                    344
         EV71 SP70

RECOMBINANT FLAVIVIRAL CONSTRUCTS AND USES THEREOF

CROSS-REFERENCE TO RELATED APPLICATION

This application is the U.S. national phase of International Application No. PCT/US2011/052379, filed Sep. 20, 2011, which designated U.S. and claims priority to U.S. Provisional Application No. 61/384,720, filed Sep. 21, 2010, the entirety of which is incorporated herein by reference.

FIELD OF THE INVENTION

The present disclosure relates generally to the field of recombinant viruses and induction of specific immunity in a host. More particularly, the disclosure relates to the use of a recombinant virus vector for presenting an exogenous polypeptide antigen to a host and thereby elicits an immune response in the host to the exogenous polypeptide antigen.

BACKGROUND OF THE INVENTION

Replicon-based expression vectors have been developed for various RNA virus families, including alphaviruses, picornaviruses and flaviviruses. For example, expression system utilizing Yellow Fever viruses (YFV) for the presentation of foreign proteins or polypeptides that act as immunogens or therapeutic agents in host cells are well known. However, expression of foreign proteins or polypeptides in the prior art expression systems or vectors is limited to the structural regions of the flaviviruses.

The present invention overcomes the disadvantages and defects of the prior expression systems or vectors in that it provides the ability for foreign proteins or polypeptides to be functionally expressed in the nonstructural region of the virus, particularly, the C-terminus of a secreted non-structure protein 1 of a flavivirus.

SUMMARY

The present invention provides recombinant viral constructs derived from flaviviruses such as Japanese encephalitis virus (JEV) and dengue viruses (DEN) and uses thereof. The recombinant viral construct encodes a fusion protein, which comprises an exogenous (i.e., non-JEV or non-DEN) polypeptide antigen and a flaviviral non-structural protein 1 (NS1) or a segment thereof. Particularly, the exogenous polypeptide antigen is inserted at the carboxyl-terminus of the flavivirus NS1, such as JEV NS1, and the production of the recombinant fusion protein does not affect viral replication. Upon infection a cell with such recombinant viral constructs, flavivirus particles comprising limited multiplicative virions (LMV) may be produced. Each LMV comprises the flaviviral replicon or genome described above. The flavivirus particles are useful in eliciting an immune response to the exogenous polypeptide in a host and thereby confer the host with protective immunization against the exogenous polypeptide.

It is therefore a first aspect of the present invention to provide an isolated recombinant viral construct for expressing an exogenous polypeptide in a cell. The isolated recombinant viral construct comprises a flaviviral replicon comprising a nucleic acid encoding a fusion protein comprising a non-structural protein 1 (NS1) or a segment thereof and the exogenous polypeptide, wherein the exogenous polypeptide is at least 6 amino acids in length and is inserted into the carboxyl-terminus of the NS1, and the production of the fusion protein does not affect viral replication.

The flaviviral replicon is a Japanese encephalitis virus (JEV) replicon or a dengue viruses (DEN) replicon. Preferably, the flaviviral replicon is JEV replicon.

In the case where the JEV replicon is employed, the JEV replicon comprises a nucleic acid encoding a fusion protein comprising, in sequence, a JEV non-structural protein 1 (JEV NS1) segment, the exogenous polypeptide, and a tail polypeptide. The JEV NS1 segment comprises at least amino acid residues 1 to 340 of the JEV NS1; the exogenous polypeptide has at least 6 amino acids; and the tail polypeptide comprises at least amino acid residues 344 to 352 of the JEV NS1.

According to some embodiments, the exogenous polypeptide comprises an immunogenic segment, such as an Enterovirus 71 (EV71) SP70 antigen, an EV71 VP1 antigen, a hepatitis B virus surface antigen or an immunogenic portion thereof. According to one embodiment, the exogenous polypeptide is at least 6 amino acids in length; and preferably at least 15 amino acids in length.

Optionally, the exogenous polypeptide may further comprise a protease segment preceding the immunogenic segment. The protease segment may comprises a Foot-and-Mouth Disease virus 2A (FMDV-2A) peptide to efficiently separate the exogenous polypeptide from the engineered NS1 fusion protein. In this embodiment, the recombinant viral construct may have a higher insertion capacity; for example, the exogenous polypeptide may be at least 50 amino acids in length; preferably at least 100 amino acids in length; and more preferably, at least 150 amino acids in length.

The flaviviral replicon comprises a promoter operable linked thereto, so that the fusion protein containing the exogenous polypeptide and the flavivirus NS1 may be expressed and subsequently secreted out of the cell. The cell may be any of a baby hamster kidney cells (e.g., BHK-21 cell), an *Aedes albopictus* C6/36 mosquito cell line (C6/36 cell), or Vero cell. Preferably, the cell is the BHK-21 cell.

The isolated recombinant viral construct may further comprise nucleic acids encoding flavivirus structural proteins (e.g., structural proteins C, prM, E and etc) required for packaging the flaviviral replicon into a flavivirus particle. Preferably, the nucleic acids encoding flavivirus structural proteins are engineered into the flavivirus genome.

It is therefore a second aspect of this invention to provide an isolated recombinant flavivirus particle, which comprises a virion unit comprising the recombinant viral construct of this invention.

It is a third aspect of this invention to provide a method of eliciting an immune response in a host. The method comprises steps of administering the isolated recombinant flavivirus particle of this invention to the host, wherein said administering provides for expression of the exogenous polypeptide that results in induction of an immune response in the host to the exogenous polypeptide. Preferably, the host is a cell or a mammal. More preferably, the mammal is a human.

In a forth aspect, the present invention relates to a cell transfected with a recombinant viral construct in accordance with the first aspect and embodiments of the present invention.

Further, in a fifth aspect of the present invention there is provided a kit for obtaining a transfected cell in accordance with the forth aspect and embodiments of the present invention. The kit comprises an isolated recombinant nucleic acid construct of the present invention and instructions for the use of said isolated recombinant construct.

BRIEF DESCRIPTION OF THE DRAWINGS

The present description will be better understood from the following detailed description read in light of the accompanying drawings, wherein.

DETAILED DESCRIPTION OF PREFERRED EMBODIMENTS

Figure 1:
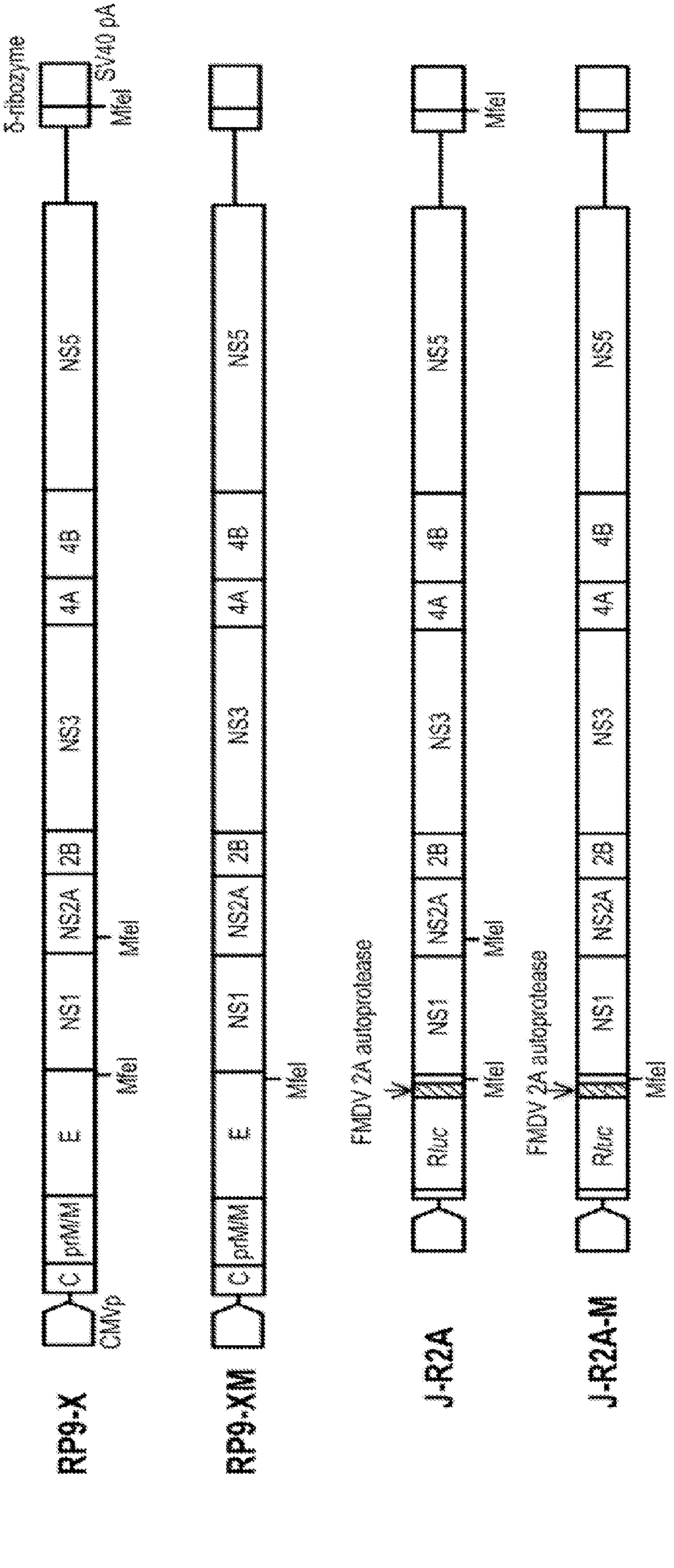
FIG. 1 is a schematic representation of the recombinant constructs of RP9-X, RP9-XM, J-R2A and J-R2A-M in accordance with one embodiment of this invention.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Throughout this specification, unless otherwise indicated, "comprise", "comprises" and "comprising" are used inclusively rather than exclusively, so that a stated integer or a group of integers may include one or more other non-stated integers or groups of integers.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, and tissue culture and transformation (e.g., lipofection). Enzymatic reactions and purification techniques are performed according to manufacturer's specifications or as commonly accomplished in the art or as described herein. The forgoing techniques and procedures are generally performed according to conventional methods well known in the art and as described in various general and more specific references that cited and discussed throughout the present specification. Standard techniques are used for pharmaceutical preparation, formulation, and delivery, and treatment of patients.

As utilized in accordance with the present disclosure, the following terms, unless otherwise indicated, shall be understood to have the following meanings:

The term "nucleic acid" as used herein designates single- or double-stranded RNA, mRNA, and DNA including cDNA and genomic DNA.

The term "polypeptide" as used herein is a general term to refer to native protein, fragments or analogs of a polypeptide sequence. Hence, native protein, fragments, and analogs are species of the polypeptide genus.

The term "recombinant" in the context of polypeptide coding regions and polypeptide encoded by such coding regions refers to non-native products wherein the coding regions, and typically the expression thereof, have been manipulated in vitro by man to differ from their occurrence in nature. The polypeptides utilized in the methods of the present invention may be produced in a number of different recombinant systems known in the art, including but not limited to, prokaryotic or eukaryotic system. For expression in an appropriate expression system, the desired viral polypeptide coding regions are operably linked to an expression vector and introduced into a host cell to enable expression. The coding region with the appropriate regulatory regions will be provided in proper orientation and reading frame to allow for expression. Methods for gene construction are known in the art. See, in particular, Molecular Cloning, A Laboratory Manual, Sambrook et al., Cold Spring Harbor Laboratory, Second Edition, Cold Spring Harbor, N.Y. (1989) and the references cited therein.

The term "isolated" is used in reference to a molecule, the term means that the molecule has been removed from its native environment. For example, a polynucleotide or a polypeptide naturally present in a living animal is not "isolated", but the same polynucleotide or polypeptide separated from the coexisting materials of its natural state is "isolated." Further, recombinant DNA molecules contained in a vector are considered isolated for the purpose of the present invention. Isolated DNA molecules include in vivo or in vitro DNA molecules. Isolated nucleic acid molecules further include synthetically produced molecules. Additionally, vector molecules contained in recombinant host cells are also isolated.

As used herein, the term "construct or vector" refers to agent (e.g., a plasmid or virus) used to transmit genetic material to a host cell. A construct or a vector may be composed of either DNA or RNA.

As used herein, the term "exogenous or heterologous polynucleotide sequence" refers to a second nucleotide sequence present in a constructor or a vector of the invention. The term "exogenous or heterologous polypeptide sequence" refers to any amino acid sequence encoded by an exogenous polynucleotide sequence contained in a vector of the invention. Heterologous polynucleotide sequence may encode proteins or RNA molecules normally expressed in cell type in which they are present or molecules not normally expressed therein.

The term "flavivirus" and "flaviviral" refer to members of the family Flaviviridae within the genus *Flavivirus*, which contains 65 or more related viral species. Typically, flavivirus are small, enveloped RNA viruses with peplomers comprising a single glycoprotein E. Other structural proteins are designated C (core) and M (membrane-like). Flaviviruses infect a wide range of vertebrates, and many are transmitted by arhropods such as ticks and mosquitoes. Particularly, non-limiting examples of flavivirus are West Nile virus (WNV), Kunjin virus, Yellow Fever virus (YFV), Japanese Encephalitis virus (JEV), Dengue virus (DEN), Usutu virus, St Louis Encephalitis virus (SLE) and tick-born encephalitis virus (TBEV). Preferably, flavivirus suitable for use in this invention are JEV and DEN.

The term "recombinant viral construct" refers to assembly which is capable of directing the expression of a sequence(s) or gene(s) of interest. Such viral constructs are comprised of a 5' sequence which is capable of initiating transcription of a viral RNA (e.g., JEV RNA), as well as sequences which, when expressed, code for biologically active viral nonstructural proteins. The viral construct may also include sequences from one or more structural and/or nonstructural protein genes or portions thereof, exogenous nucleic acid molecules which are of a size sufficient to allow production of viable virus, a 5' promoter which is capable of initiating the synthesis of viral RNA in vitro from cDNA, an exogenous sequence to be expressed, as well as one or more restriction sites for insertion of heterologous sequences.

The term "replicon" refers to a viral DNA or RNA molecule that is capable of directing its own amplification or self-replication in vivo, within a target cell. To direct its own replication, the DNA or RNA molecule may: (1) encode one or more polymerase, replicase, or other proteins which may interact with viral or host cell-derived proteins, nucleic acids or ribonucleoproteins to catalyze DNA or RNA amplification; and (2) contain cis DNA or RNA sequences required for replication which may be bound by its self-encoded proteins, or non-self-encoded proteins, cell-derived proteins, nucleic acids or ribonucleoproteins, or complexes between any of these components. Flavivirus replicon RNA produced in cells as a result of its self-amplification either after RNA transfection or after plasmid DNA transfection, can be packaged into the secreted virus-like particles (VLPs) by providing structural proteins from a second vector.

The present invention, at least in part, arises from the unexpected finding that the C-terminus portion of non-structural protein 1 (NS-1) of a flavivirus (e.g., JEV) may tolerate exogenous polypeptide insertion, hence may serve as a good vehicle for presenting foreign epitope(s) to a host. Furthermore, the inclusion of the exogenous polypeptide within the flaviviral replicon does not significantly reduce replication capability of the flaviviral replicon.

It will be appreciated that the present invention contemplates a recombinant viral construct capable of presenting an immunogenic epitope of a virulent and/or pathogenic virus to a host to protectively immunize the host against said virulent and/or pathogenic virus. The invention may therefore be useful in human and veterinary medicine.

Therefore, in a preferred embodiment, the invention provides an isolated recombinant viral construct for expressing an exogenous polypeptide in a cell. The isolated recombinant viral construct comprises a JEV replicon comprising a nucleic acid encoding a fusion protein that comprises a JEV non-structural protein 1 (JEV NS1) or a segment thereof and an exogenous polypeptide, wherein the exogenous polypeptide is at least 6 amino acids in length and is inserted into the carboxyl-terminus of the JEV NS1, wherein the production of the exogenous polypeptide does not affect viral replication.

Specifically, the fusion protein comprises, in sequence, a JEV non-structural protein 1 (JEV NS1) segment, the exogenous polypeptide, and a tail polypeptide. Generally, the exogenous polypeptide has at least 6 amino acids, preferably, at least 15 amino acids; more preferable, at least 50 amino acids. In particular, the exogenous polypeptide to be inserted therein could have at least 6, 10, 15, 20, 30, 40, 50, 60, 70, 80, 90, or 100 amino acids. For example, some exogenous polypeptides described in the Examples hereinbelow each have a length of 22, 39, 56 and 73 amino acids.

The JEV NS1 segment comprises at least amino acid residues 1 to 340 of the JEV NS1, and the tail polypeptide comprises at least amino acid residues 344 to 352 of the JEV NS1. Throughout the present disclosure, a JEV NS1 segment comprising amino acid residues 1 to n of the JEV NS1 is denoted as JEV $NS1_n$, whereas a tail polypeptide comprising amino acid residues m to 352 of the JEV NS1 is denoted as tail $polypeptide_m$.

According to one embodiment of the present disclosure, the fusion protein comprises a JEV $NS1_{340}$, an exogenous polypeptide, and a tail $polypeptide_{341}$, such as the cDNA clone $_{340341}$SP70 described hereinbelow. In another embodiment, the fusion protein comprises a JEV $NS1_{343}$, an exogenous polypeptide, and a tail $polypeptide_{344}$, such as the cDNA clone $_{343344}$SP70 described hereinbelow. In still another embodiment, the fusion protein comprises a JEV $NS1_{340}$, an exogenous polypeptide, and a tail $polypeptide_{344}$, such as the cDNA clone $_{340344}$SP70 described hereinbelow.

Without being bound by theory, it is believed that the presence of the consecutive amino acid residues 344 to 352 of the JEV NS1 at the end of the fusion protein is required for the expression and secretion of the fusion protein. Accordingly, in one embodiment, the fusion protein comprises a JEV $NS1_{352}$, an exogenous polypeptide, and a tail $polypeptide_{344}$, such as the cDNA clone $_{352344}$SP70 described hereinbelow.

In some cases, the presence of the consecutive amino acid residues 341 to 352 of the JEV NS1 at the end of the fusion protein is preferred. Therefore, the fusion protein comprises a JEV $NS1_{343}$, an exogenous polypeptide, and a tail $polypeptide_{341}$, such as the cDNA clone $_{343341}$SP70 described hereinbelow. In another embodiment, the fusion protein comprises a JEV $NS1_{352}$, an exogenous polypeptide, and a tail $polypeptide_{341}$, such as the cDNA clone $_{352341}$SP70 described hereinbelow.

According to the principles and spirits of the present disclosure, the exogenous polypeptide comprises an immunogenic segment, such as an EV71 SP70 antigen, an EV71 VP1 antigen, or an immunogenic portion thereof. According to one embodiment, the exogenous polypeptide is at least 6 amino acids in length; and preferably at least 15 amino acids in length. As a non-limiting example, the exogenous polypeptide is EV71 SP70 antigen having an amino acid sequence of YPTFGEHKQEKDLEY (SEQ ID NO: 10), which is 15 amino acids in length. In one embodiment, EV71 SP70 antigen sequence of galYPTFGEHKQEKDLEYasra (SEQ ID NO: 11), which is 22 amino acids in length including linker sequence in lowercase letter, is inserted between the JEV $NS1_{343}$ and the tail $polypeptide_{344}$. In other embodiments, immunogenic segments comprising 2, 3 or 4 copies of the above-described EV71 SP70 antigen sequence of YPTFGEHKQEKDLEY (SEQ ID NO: 10), which are 39, 56 and 73 amino acids in length, respectively, were inserted between the JEV $NS1_{343}$ and the tail $polypeptide_{344}$, with reduced viral replication or infection.

In optional embodiments, the exogenous polypeptide may further comprise a protease segment preceding the immunogenic segment thereby providing a recombinant viral construct that has a higher insertion capacity. The protease segment may comprise a Foot-and-Mouth Disease virus 2A (FMDV-2A) peptide. In this embodiment, the thus-obtained recombinant viral construct is capable of carrying an exogenous polypeptide having at least 100 amino acids in length. In particular, the exogenous polypeptide to be inserted therein could have a length of at least 100, 110, 120, 130, 140, 150, 160, 170, 180, 190, 200, 210, 220, 230, 240, or 250 amino acids. For example, two exogenous polypeptides described in the Examples hereinbelow each have a length of 153 and 202 amino acids.

Still optionally, the exogenous polypeptide may further comprise a secretion-signal segment between the protease segment and the immunogenic segment, wherein the secretion-signal segment comprises a secretion signal peptide derived from *Gaussia* luciferase.

In one exemplary embodiment, the exogenous polypeptide has a total length of 153 amino acids that consists of an FMDV-2A peptide (NFDLLKLAGDVESNPGP, 17 amino acids), a secretion signal peptide derived from *Gaussia* luciferase (MGVKVLFALICIAVAEAGL, 19 amino acids), and amino acid 145th to 261st from EV71 VP1 (117 amino acids). The exogenous polypeptide was inserted between the JEV $NS1_{343}$ and the tail $polypeptide_{344}$. A suitable promoter is operably linked to the replicon so as to facilitate the amplification or self-replication of the viral replicon and the exogenous polypeptide linked thereto in the host cell. Suitable promoters include, but are not limited to, mammalian-operable promoters inducible through the bacterial lac operon (e.g., lac-regulated CMV or RSV promoter). A preferred promoter is a CMV promoter.

The host cell suitable for receiving the recombinant viral construct of this invention may be any of a BHK-21 cell, a C6/36 cell, a Vero cell, or other equivalent mammalian cells. Preferably, the host cell is a BHK-21 cell.

The present invention is characterized in that it provides the ability for exogenous proteins or polypeptides to be functionally expressed in the nonstructural region of the virus, particularly, nonstructural protein 1 (NS1) of a flavivirus. Nonstructural protein 1 contains two distinct domains or regions, and their precise roles in viral replication are not yet well understood. The C-terminus region is not conserved among known flaviviruses in length or in sequence, and multiple changes are tolerated. Insertion/deletion studies on the C-terminus region of JEV NS1 have been conducted in accordance with one example of this invention. The exogenous polypeptide having at least 6 amino acids may be inserted into the carboxyl-terminus of the NS1.

Figure 4:
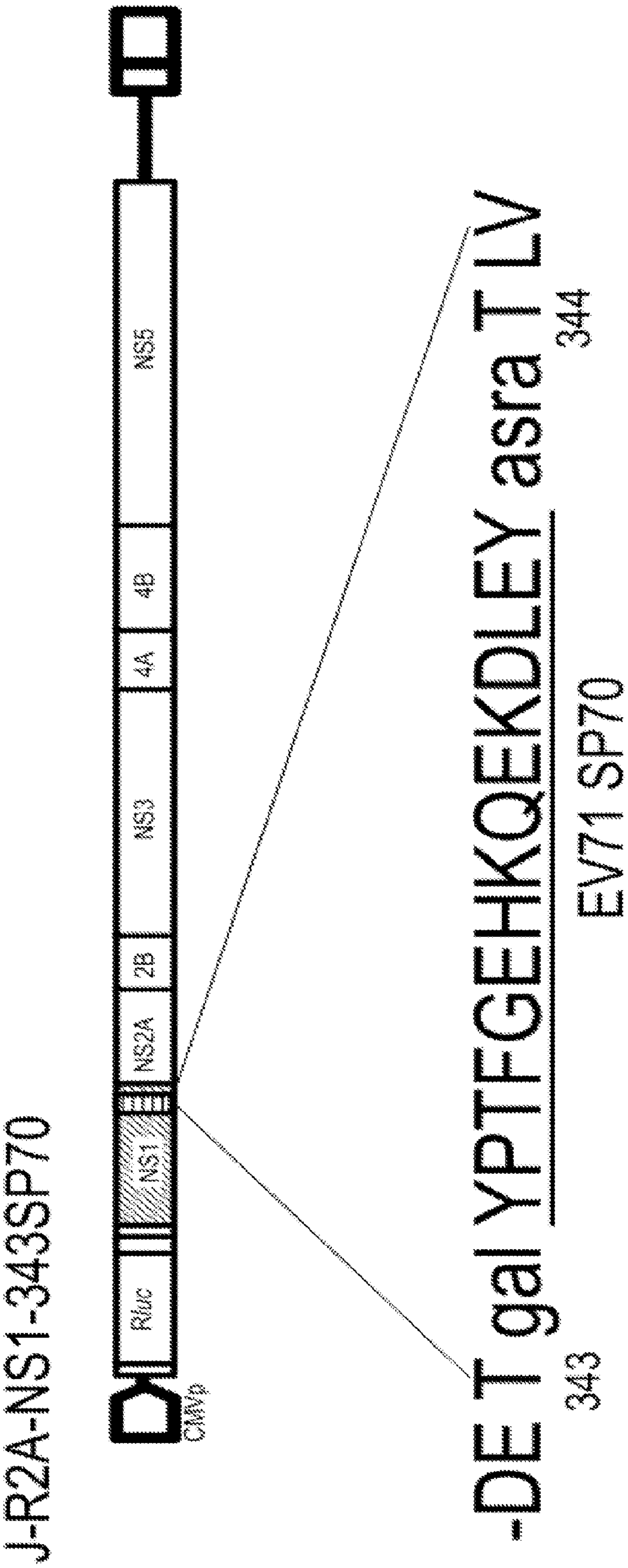
FIG. 4 is a schematic representation of the recombinant JEV construct (i.e., J-R2A-NS1-343SP70) having an Enterovirus 71 (EV71) SP70 antigen with linker (galYPTFGEHKQEKDLEYasra, SEQ ID NO: 11) inserted between residues 343 and 344 of JEV NS1 (SEQ ID NO: 16) in accordance with one embodiment of this invention.
Figure 8:
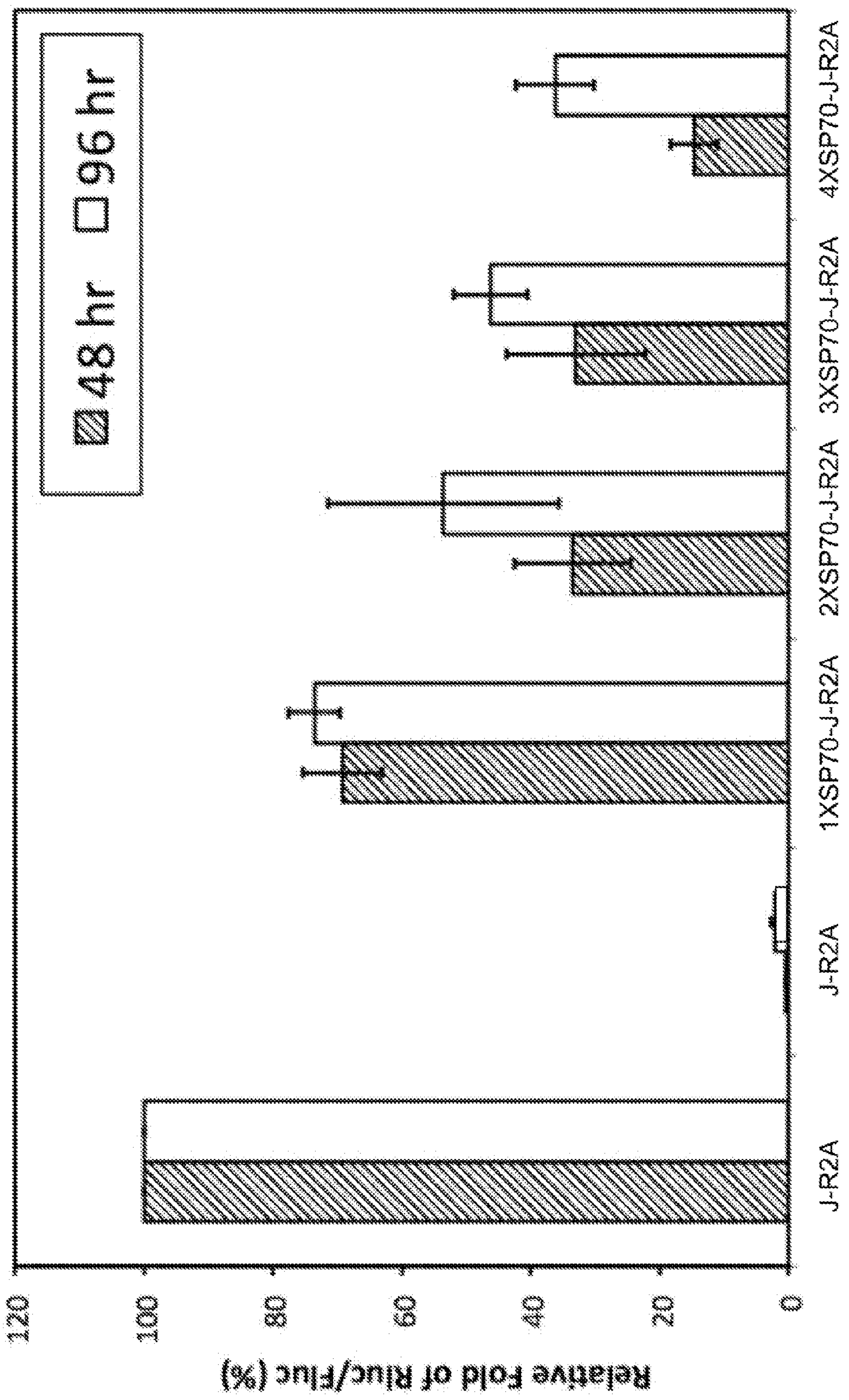
FIG. 8 depicts the replication ability of the recombinant replicons capable of expressing fusion proteins comprising 1, 2, 3 and 4 copies of EV71 SP70 epitopes, respectively; and analyzed by trans-complementation assays in accordance with one embodiment of this invention.

In one embodiment, Enterovirus 71 (EV71) SP70 antigen sequence of galYPTFGEHKQEKDLEYasra (SEQ ID NO: 11), which is 22 amino acids in length including linker sequence in lowercase letter, is inserted between the JEV $NS1_{343}$ and the tail $polypeptide_{344}$ (FIG. 4). In other embodiments, immunogenic segments comprising 2, 3 or 4 copies of the above described Enterovirus 71 (EV71) SP70 antigen sequence of YPTFGEHKQEKDLEY (SEQ ID NO: 10), which are 39 (SEQ ID NO: 12), 56 (SEQ ID NO: 13) and 73 (SEQ ID NO: 14) amino acids in length, respectively were inserted between the JEV $NS1_{343}$ and the tail $polypeptide_{344}$, with reduced viral replication or infection (FIG. 8). The isolated recombinant viral construct may further comprise nucleic acids encoding flavivirus structural proteins (e.g., structural proteins C, prM and E) required for packaging the flaviviral replicon of this invention into a flavivirus particle. Such nucleic acids are preferably engineered into the flaviviral genome.

Therefore, in a preferred embodiment, the invention provides an isolated recombinant flavivirus particle, comprising a virion unit comprising the isolated recombinant viral construct of this invention. The virion may be used as an immunogen (e.g., a live or killed vaccine) for eliciting a protective immune response to at least the exogenous polypeptide encoded by the flavivirus replicon of this invention in a subject. Accordingly, an immunotherapeutic composition or vaccine may be produced. The immunotherapeutic composition or vaccine may be used to prophylatically or therapeutically immunize animals such as human.

It is therefore a further aspect of this invention to provide a method of eliciting an immune response in a subject. The method comprises steps of administering the isolated recombinant flavivirus particle of this invention to the subject, wherein said administering provides for expression of the exogenous polypeptide that results in induction of an immune response in the subject to the exogenous polypeptide. The subject may be a vertebrate animal such as cows, sheep, dogs, cats, birds, pigs and etc. In other embodiment, the vertebrate animal is a mammal. More preferably, the mammal is a human.

In certain embodiments, it is contemplated that a transfected cell comprises a recombinant viral construct of the invention. The transfected cell is a cell type that can be used to express the exogenous polypeptide encoded by the construct. For examples, it is known that JEV vectors may be used to express exogenous polypeptides in mammalian cells, examples of which include, but are not limited to, BHK-21 cells and C6/36 cells; preferably, BHK-21 cells.

The present invention is also directed to a kit that supplies the elements necessary to conduct transfection of cells. The kit comprises an isolated recombinant viral construct of the invention and instructions for the use of said isolated recombinant construct.

In one embodiment, a kit for inserting a DNA sequence of interest into a recombinant viral construct is provided. The recombinant viral construct comprises a first nucleic acid sequence and a second nucleic acid sequence operably linked to the first nucleic acid sequence. The first nucleic acid sequence encodes a JEV NS1 segment comprising at least amino acid residues 1 to 340 of the JEV NS1, whereas the second nucleic acid sequence encodes a tail polypeptide comprising at least amino acid residues 344 to 352 of the JEV NS1. The DNA sequence of interest may be inserted between the first and second nucleic acid sequences in accordance with instructions provided with the kit to obtain the recombinant viral construct for expressing an exogenous polypeptide in a cell. In one optional embodiment, the kit may further comprise a third nucleic acid sequence positioned between the first and second nucleic acid sequences. The third nucleic acid sequence encodes an FMDV-2A peptide, and the DNA sequence of interest may be inserted between the third and second nucleic acid sequences in accordance with instructions provided with the kit to obtain the recombinant viral construct for expressing an exogenous polypeptide in a cell.

Alternatively, the DNA sequence of interest could be inserted into a recombinant viral construct in advanced. In this case, a kit comprising a recombinant viral construct for expressing an exogenous polypeptide in a cell is provided together with instructions for using the same. In one embodiment, the recombinant viral construct for expressing an exogenous polypeptide in a cell comprises, in sequence, the first nucleic acid sequence, the DNA sequence of interest, and the second nucleic acid sequence. In one optional embodiment, the recombinant viral construct for expressing an exogenous polypeptide in a cell comprises, in sequence, the first nucleic acid sequence, the third nucleic acid sequence, the DNA sequence of interest, and the second nucleic acid sequence.

In certain embodiments, any of the above mentioned kits may optionally comprise cells suitable to be infected by the recombinant viral construct.

Said instructions for the use of said isolated recombinant construct may include instructions as to the amount or concentration of the isolated recombinant viral construct provided. If the construct is provided dried, the instructions may teach how to reconstitute the construct into solution. The instructions may further teach how to introduce said construct into a cell. Additionally, the instructions can indicate various cell types that can be transfected with the construct and how to culture the transfected cells so that they will express a desired exogenous polypeptide. The instructions may also teach how to recover the desired exogenous polypeptide from a transfected cell or from a conditioned cell culture medium produced by a transfected cell. Instructions may be included in the kit in either printed or electronic form. Alternatively, the instructions can be provided by way of a link or internet address that provides access to instructions located on either an internet or extranet site. The internet site can be either publicly available or secure.

The individual components of the kits can be packaged in a variety of containers, e.g., vials, tubes, microtiter well plates, bottles, and the like. Other reagents can be included in separate containers and provided with the kit; e.g., positive control samples, negative control samples, buffers, cell culture media, etc.

Numerous aspects and advantages of the invention will be apparent to those skilled in the art upon consideration of the following detailed description which provides illumination of the practice of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiment bellow are all or the only experiments performed. Efforts have been made to ensure accuracy with respect to numbers used (e.g., amounts, temperature and etc.) but some experimental errors and deviations should be accounted for.

Example 1

Generating Recombinant Japanese Encephalitis Viral (JEV) Constructs

The JEV replicon J-R2A was constructed by steps as described below. CMV-RP-9-ribo-polyA/pBR322, a full-length infectious cDNA clone of Japanese encephalitis virus of Taiwan strain (RP-9, National Center for Biotechnology Information (NCBI) access No: AF014161; SEQ ID NO: 15) was prepared in accordance with the method described previously by Liang et al (Vaccine (2009) 27: 2746-2754). This cDNA clone was used to construct JEV replicon, J-R2A (FIG. 1), in which structure genes of C-prM-E were removed and replaced by *Renilla* luciferase gene using jumping polymerase chain reaction (PCR). An FMDV-2A peptide sequence was then inserted behind the reporter gene so that *Renilla* luciferase may be precisely spliced with non-structure proteins after translation. Briefly, the C-prM-E gene of JEV cDNA clone was truncated using PCR. Primer prJE2388ApaKpnF (SEQ ID NO: 1,5'-gagggcccatggtacc atgggcgtcaacgcacga-3') and primer JE4507-4489 (−) (SEQ ID NO: 2,5'-cagaccttccatggaacac-3') was used to amplify JEV partial E to NS2 fragment; and the amplified product was placed into the C-prM-E portion of CMV-RP-9-ribo-polyA/pBR322 after ApaI and XmaI digestion. Then, *Renilla* luciferase gene was amplified using primers prJE181-197-AgeI-RLuc (SEQ ID NO: 3,5'-cataaactttcgaagtcataccggttac-tacc-ctcttcactc-3'), prJE1-25-F (SEQ ID NO: 4,5'-agaagtt-tatctgtgtgaacttctt-3') and prRLuc-NotKpnR (SEQ ID NO: 5,5'-ctggtaccggcggccgcttgttcatttttgagaactc-3') to restore partial Capsid for replication required CS sequence. After ApaI and KpnI digestion, the PCR product was inserted into the C-prM-E deleted cDNA clone. Finally, FMDV 2A peptide sequence was introduced into the construct by PCR amplification using primers prFMDV2A_F (SEQ ID NO: 6,5'-gctagcggccgccaacttcgacctcctcaagttggcgggagacg-3') and prFMDV2A_R (SEQ ID NO: 7,5'-ctggtacccggcccagggttg-gactcaacgtctcccgccaacttg-3'). After NotI and KpnI digestion, FMDV 2A sequence was inserted into above described cDNA clone and denoted as J-R2A (FIG. 1).

J-R2A-M replicon was generated from J-R2A replicon by single-primer mutation, in which MfeI sites were silently removed with primers prJE_SP_NS2A__3856-3897(+) (SEQ ID NO: 8, 5'-tcctaggggctgccttttccagttagcctcagt-agatctgc-3') and prR2A_SP_polyA__10106-10147(+) (SEQ ID NO: 9, 5'-tgaacctgaaacataaaatgaatgcagttgttgttgttaacttgtt-3'). The MfeI site at NS2A of J-R2A and MfeI site at delta ribozyme were both removed. The Infectious clone of RP9-XM was also constructed by replacing the corresponding region of J-R2A-M (FIG. 1), and the infectivity of virus recovered from RP9-XM was found to be similar to that from the parental RP9-X in mouse experiments.

Example 2

Characterization of the JEV NS1 Functionality by Use of NS1 C-terminal Truncated Mutants of J-R2A of Example 1

To study the relationship between JEV NS1 C-terminal amino acid and the NS1 functionality, several defective replicons J-R2A-dNS1 (i.e., NS1 C-terminal truncated mutants of J-R2A of Example 1) were generated and NS1 functionality of each defective replicon was analyzed by trans-complementation assays. Specifically, J-R2A-dNS1, and series of NS1 C-terminus truncated mutants including J-NS1.332/pCR3.1, J-NS1.337/pCR3.1, J-NS1.342/pCR3.1, and J-NS1.344/pCR3.1 were constructed. Each of the J-NS1 C-terminus truncated clones was subjected to trans-complementation assay, and 96 hrs after transfection, cell lysate of each clone was collected and replication ability of each clone was quantified by dual luciferase assay.

Briefly, 0.3 µg of each recombinant replicon DNA and 0.03 µg of pGL3 plasmid DNA, which served as the internal control, were mixed with 1.5 µl of Lipofectamine 2000 (Invitrogen, USA), and the mixture was used to transfect BHK-21 cells that were in 50-60% confluence in each well of the 24-well culture plate. For trans-complementation assay, 0.3 µg of recombinant J-NS1.flag/pCR3.1 plasmid DNA, 0.3 µg of replicon DNA, plus 0.03 µg of pGL3 plasmid DNA were mixed with Lipofectamine 2000 (Invitrogen, USA) and the mixture was used to co-transfect BHK-21 cells by steps as described above. 48 or 96 hrs after transfection, cell lysate of each clone was collected and luciferase activity of each clone was measured with commercial kits (Promega, Madison, Wis., USA) in accordance with the manufacturer's protocol. Results are depicted in FIG. 2.

Figure 2:
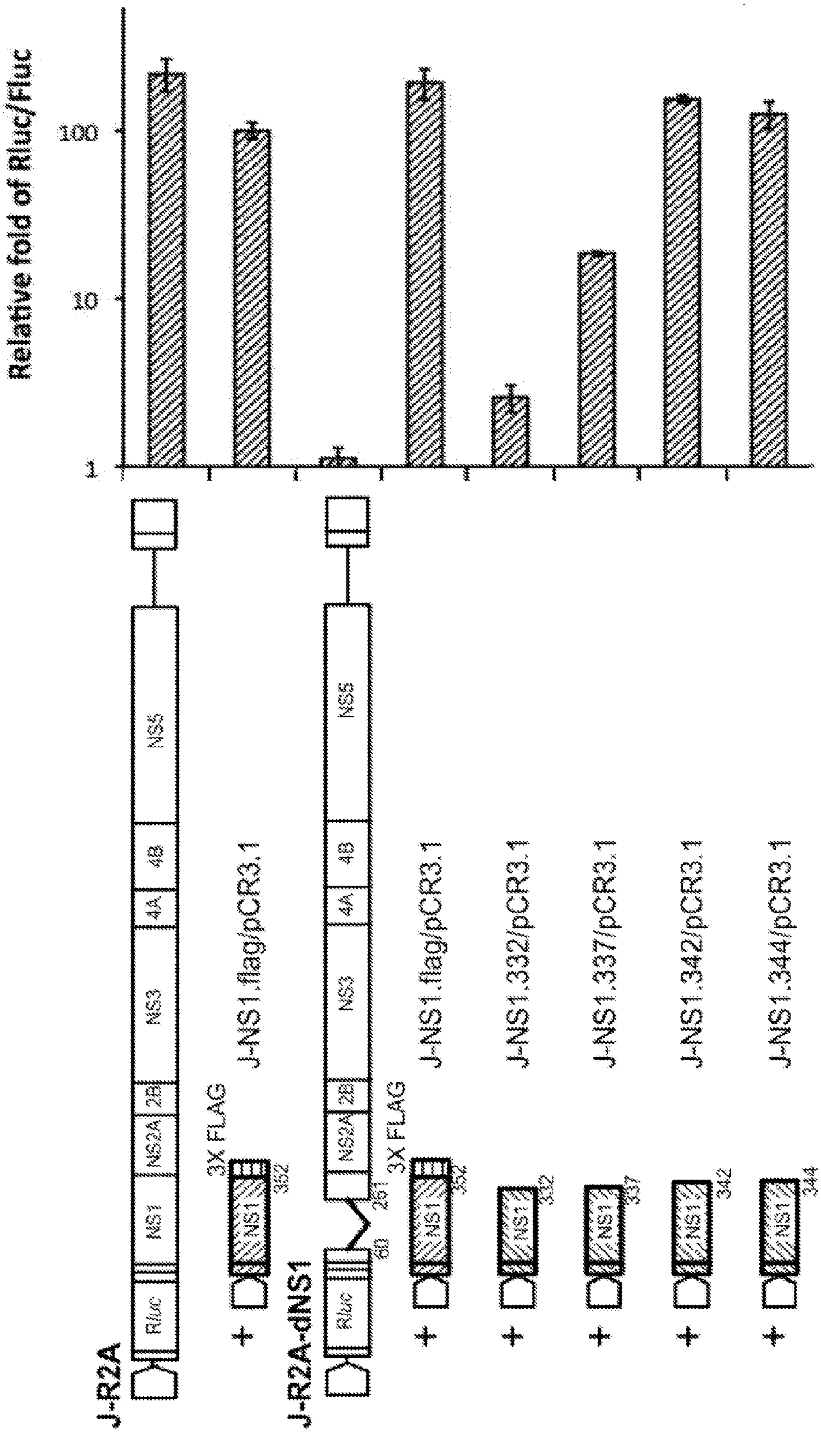
FIG. 2 depicts the effects of deletion in the C-terminus region of NS1 on viral replication ability analyzed by trans-complementation assays in accordance with one embodiment of this invention.

J-R2A-dNS1 was a NS1 deletion mutant, in which 61-260 amino acids of NS1 were deleted, and it was found that such deletion resulted in the lost of viral replication capability (FIG. 2). On the other hand, if J-R2A-dNS1 was trans complemented with J-NS1.flag/pCR3.1, which expressed JEV NS1 protein by the CMV promoter, viral replication ability was restored (FIG. 2). Further, it was found that the C-terminal truncated mutant J-NS1.332/pCR3.1 failed in trans-complementation assay; and truncated mutants J-NS1.337/pCR3.1 showed reduced replication ability; whereas truncated mutants of J-NS1.342/pCR3.1 or J-NS1.344/pCR3.1 expressed complement replication ability in trans that was comparable to that of J-NS1.flag/pCR3.1.

Therefore, JEV NS1 (SEQ ID NO: 16), which is 352 amino acids in full length, requires at least 342 amino acids to render NS1 functional, shortening NS1 C-terminus may impair its replication ability. While very C-terminal 8 amino acids of NS1 is required for poly-protein processing to separate NS1 and NS2A (Falgout and Markoff, (1995) J Virol 69: 7232-7243), it is plausible that exogenous peptide may be inserted between 342 to 344 amino acid of the NS1 protein.

Example 3

Figure 3:
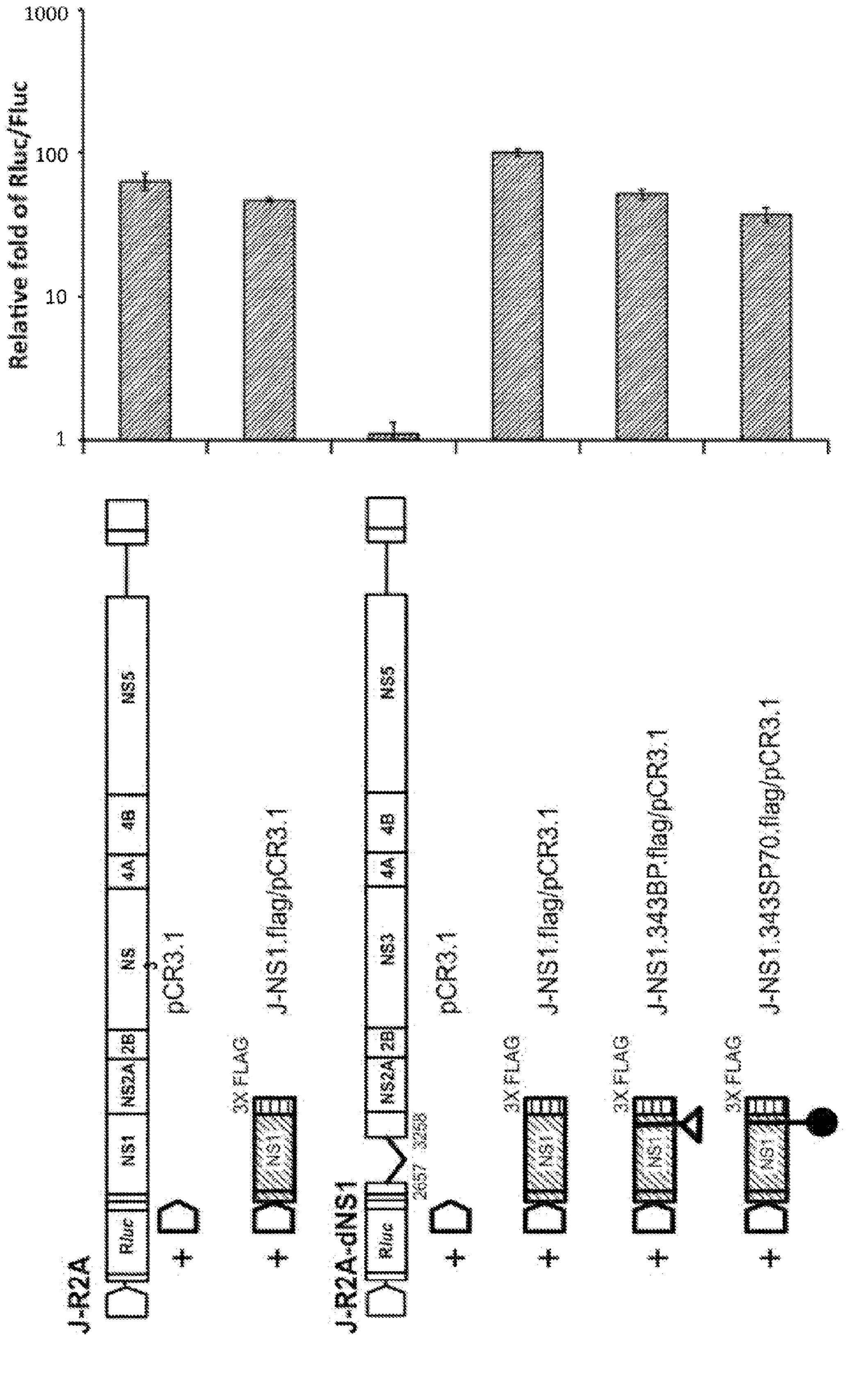
FIG. 3 depicts the replication ability of the recombinant JEV virus, which comprises an Enterovirus 71 (EV71) SP70 antigen inserted between residues 343 and 344 of JEV NS1, analyzed by trans-complementation assays in accordance with one embodiment of this invention.

Producing Fusion Protein Comprising JEV NS1 and Enterovirus 71 (EV71) SP70 Epitope In this example, two restriction sites BssHII and PmlI were first introduced into NS1 C-terminus amino acids 343 and 344 by single-primer mutagenesis, and the construct was denoted as J-NS1.BP.flag/pCR3.1. Replication ability of such clone was slightly lower than that of J-NS1.flag/pCR3.1 in trans-complementation assay. Meanwhile, an exogenous peptide, Enterovirus 71 (EV71) SP70 epitope (YPTFGEHKQEKDLEY) (Foo et al., (2007) Virus Res 125: 61-68) was inserted into the above-described J-NS1.BP.flag/pCR3.1, and the resulted clone was denoted as J-NS1.EV71.flag/pCR3.1. The replication ability of the EV71 SP70 fused J-NS1.343SP70.flag/pCR3.1 clone was found to reduce to about 50% in trans-complementation assay (FIG. 3). This reduction in replication ability may be due to the lengthening of C-terminus of NS1 or the conformational changes of the NS1.

Figure 5:
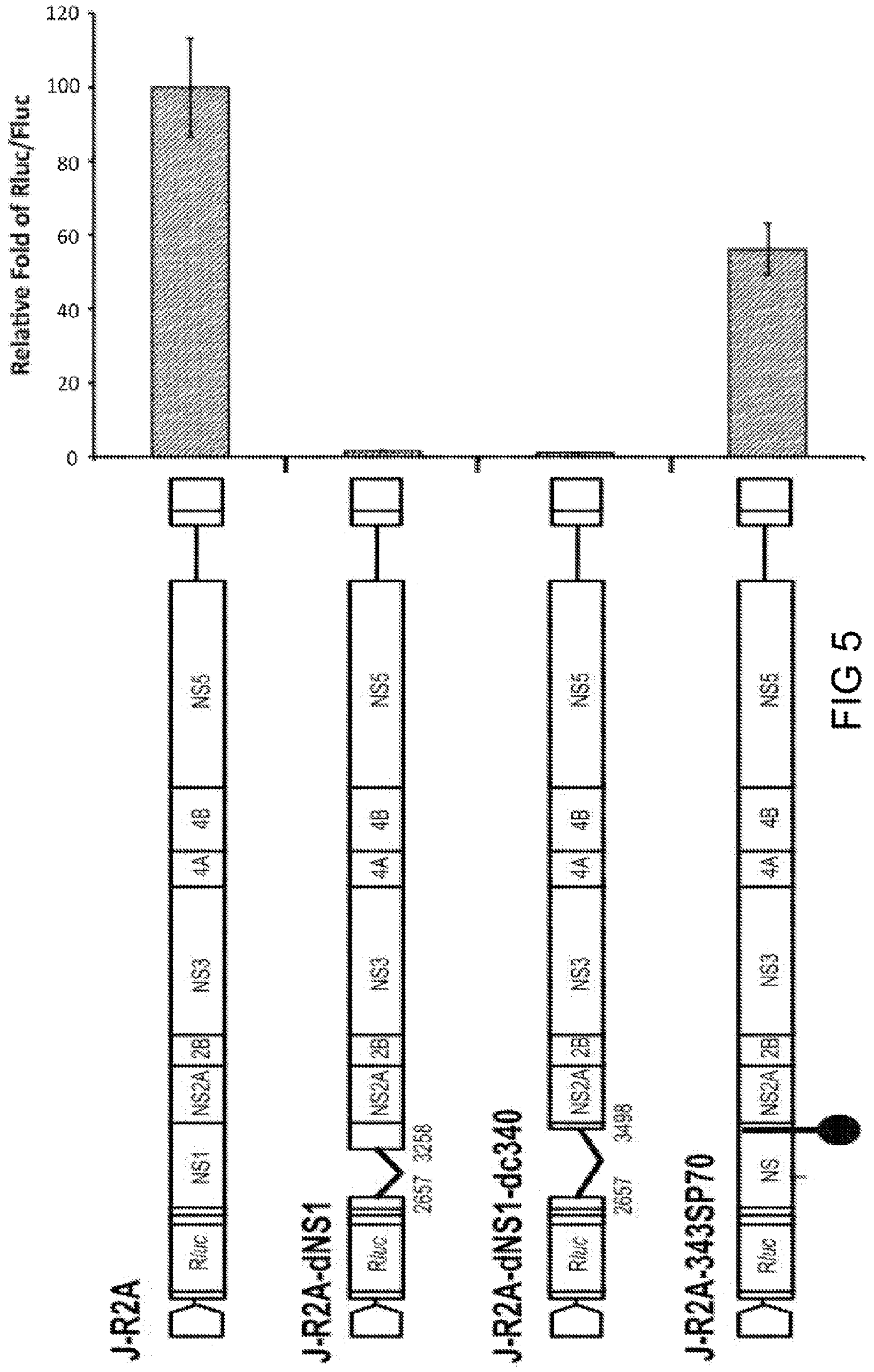
FIG. 5 depicts the replication ability of defective replicons J-R2A-dNS1 including J-R2A-dNS1, J-R2A-dNS1-dc340 and J-R2A-NS1-343SP70 analyzed by trans-complementation assays in accordance with one embodiment of this invention.

Further, J-R2A-343SP70 (FIG. 4) was constructed by common cloning techniques, including restriction enzyme digestion and ligation. In J-R2A-343SP70 clone, the EV71 SP70 was inserted between the JEV $NS1_{343}$ and the tail polypeptide$_{344}$. After verifying the sequence, plasmid DNA of J-R2A-343SP70 and J-R2A were transfected into the BHK-21 cells, the replication capabilities were quantified by dual luciferase assay system as described above. It was found that the J-R2A-343SP70 exhibited 50% replication activity of the parental J-R2A (FIG. 5), which indicates that the NS1 having an inserted EV71 SP70 epitope closed to its C-terminus has slightly effect on virus replication using replicon system.

Figure 6:
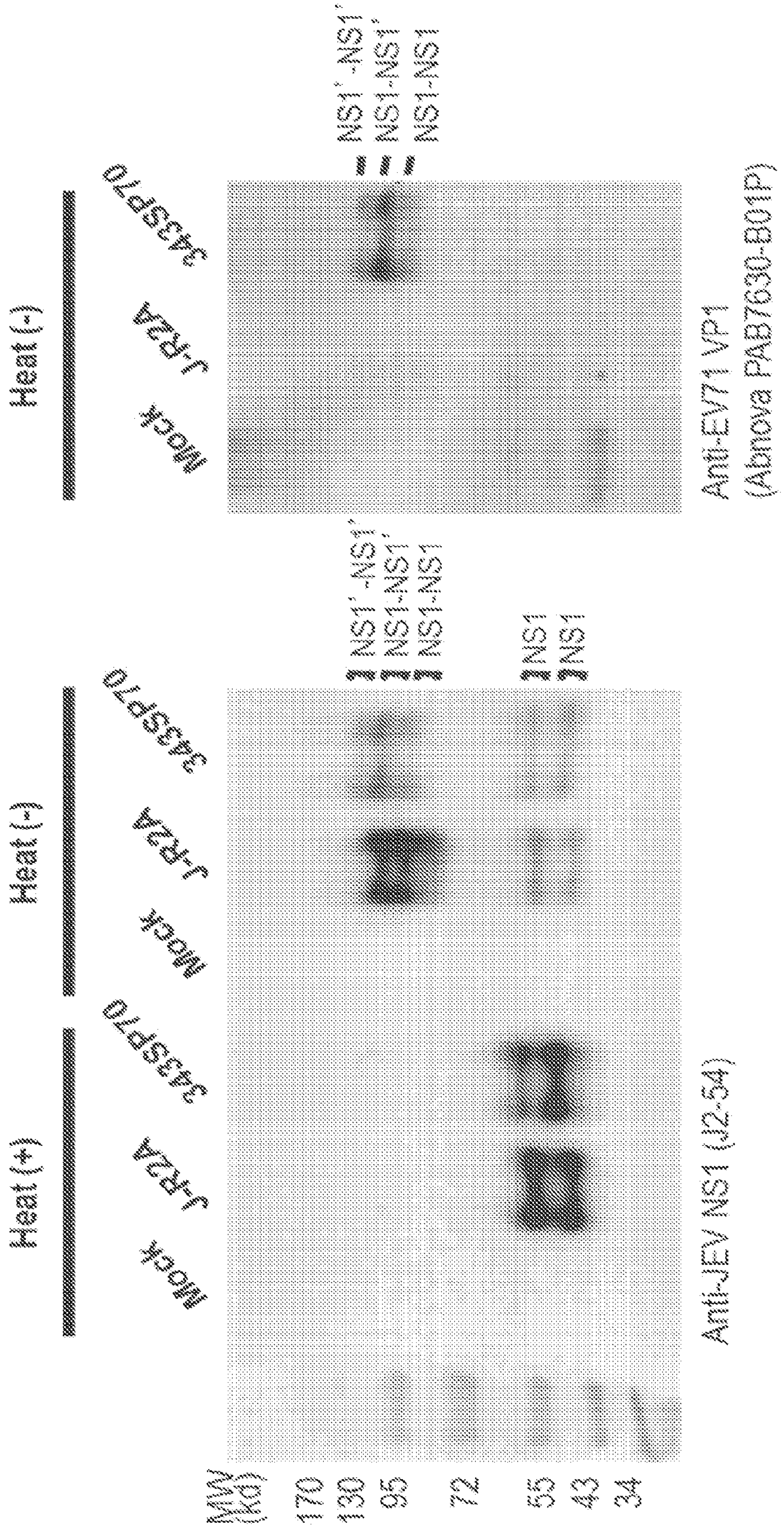
FIG. 6 depicts the expression of the fusion protein (i.e., 343SP70) by the recombinant JEV virus in BHK-21 cells analyzed by western blot in accordance with one embodiment of this invention.

Western blots were also performed to verify the expression of the fusion protein. Briefly, specific antiserum against JEV NS1 and EV71 VP1 respectively by J2-54 and PAB7630-B01P (Abnova Corp, USA) were used in this western blot assay. The transfected BHK-21 cells were treated with passive lysis buffer (Promega, Madison, Wis., USA) and total protein lysate was collected; 10% PAGE was then performed and transferred to PVDF membrane. Results are depicted in FIG. 6.

The anti J-NS1 antiserum exhibited specific binding to the monomer J-NS1, homo-dimer J-NS1 protein, as well as hetero-dimer of J-NS1 and J-NS1'. Results from FIG. 6 confirmed that NS1 may form dimers, and the dimerized NS1 has a molecular weight corresponds to that of EV71 SP70 epitope fused J-NS1, when compared with that of the authentic J-NS1 and protein size markers. The polyclonal PAB7630-B01P specifically recognized the dimeric J-NS1 proteins that fused with the EV71 SP70 epitope, instead of the authentic J-NS1 per se. These results demonstrate that the EV71 SP70 epitope may be fused with the JNS1 C-terminal, and subsequently be expressed in the live cells.

Figure 7:
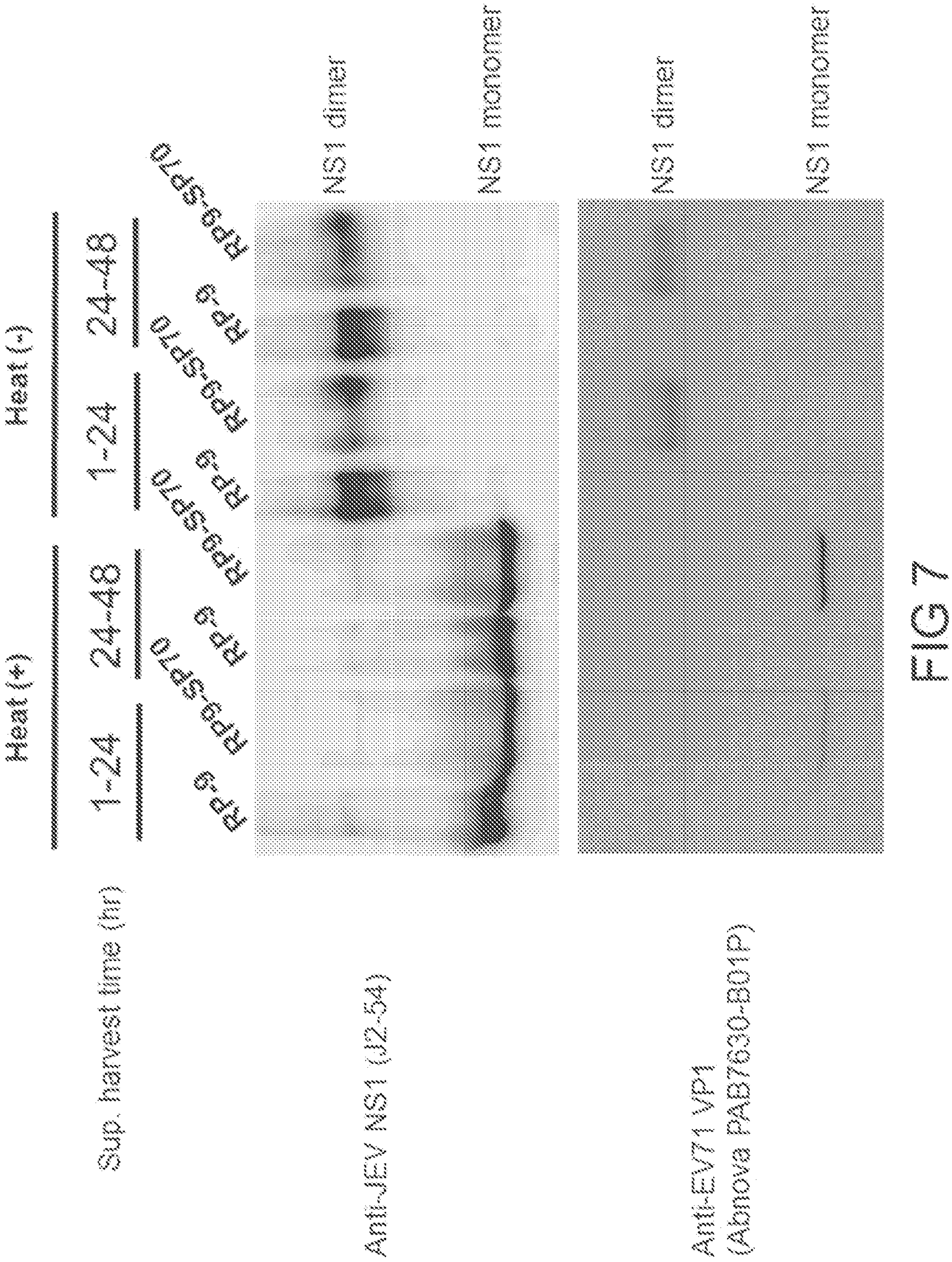
FIG. 7 depicts the secretion ability of the expressed fusion protein (i.e., 343SP70) analyzed by western blot in accordance with one embodiment of this invention.

Furthermore, the infectious clone of JEV with EV71 SP70 fused at NS1 (RP9-SP70) was constructed, recombinant RP9-SP70 virus was generated, and then was used to infect BHK-21 cells. The culture medium of BHK-21 cells were collected and concentrated using PALL Nanosep device (MWCO=10K), so as to exam the secretion ability of NS1. After 10% PAGE separation and blotting to PVDF membrane, Western blots were performed with anti-JEV NS1 monoclonal antibody and anti-EV71 VP1 polyclonal antibody; the results are illustrated in FIG. 7.

It is confirmed that the recombinant JEV NS1-SP70 can be secreted into the culture medium just as the control virus RP-9, and the recombinant JEV NS1-SP70 also exists in dimeric form of the secreted NS1 fusion proteins.

Taken together, results from this example demonstrate that the recombinant JEV infectious clone, in which the NS1 C-terminus acts as a foreign peptide carrier, can be successfully expressed and secreted out of the infected cells.

Example 4

Producing Fusion Proteins Comprising JEV NS1 and Multiple Enterovirus 71 (EV71) SP70 Epitope In this example, fusion proteins having 2, 3, and 4 copies of EV 71 SP70 epitopes, respectively, were produced according to similar procedures described in Example 3.

It is known that the J-R2A-343SP70 (1XSP70-J-R2A) construct contains a unique BssHII restriction site at 5' end of EV71-SP70 DNA sequence, and MluI and PmII restriction sites at the 3' end. While the BssHII and MluI are compatible restriction sites that can be ligated to each other, BssHII and PmII double digested EV71-SP70 PCR product as previously described were ligated to J-R2A-NS1-SP70, which was MluI and PmII digested. When BssHII and MluI are ligated, both restriction sites would be destroyed and thereby resulted in Ala-Leu di-amino acids between the EV71 SP70 epitopes. The resulted clone was therefore denoted 2XSP70-J-R2A. Meanwhile, 3XSP70-J-R2A and 4XSP70-J-R2A were also cloned. In this experiment, there are were 22, 39, 56 and 73 amino acids (SEQ ID NOs: 11, 12, 13, and 14, respectively) inserted between the JEV $NS1_{343}$ and the tail $polypeptide_{344}$ of 1XSP70-J-R2A, 2XSP70-J-R2A, 3XSP70-J-R2A and 4XSP70-J-R2A, respectively. The sequences of multiple EV71-SP70 clones were verified, and the plasmid DNA of multiple EV71-SP70 replicon clones were transfected into BHK-21 cells and subsequently verified by dual-luciferase assay. Results were depicted in FIG. 8.

FIG. 8 illustrated that the replication activity of 2×SP70-J-R2A and 3×SP70-J-R2A was about 50% of that of J-R2A after 96-hours post transfection; whereas the replication activity of 4×SP70-J-R2A was less than 40% of that of J-R2A at 96-hour post transfection.

Example 5

Survival Plot of Animals Inoculated with 343SP70 Recombinant JEV Viruses

Figure 9:
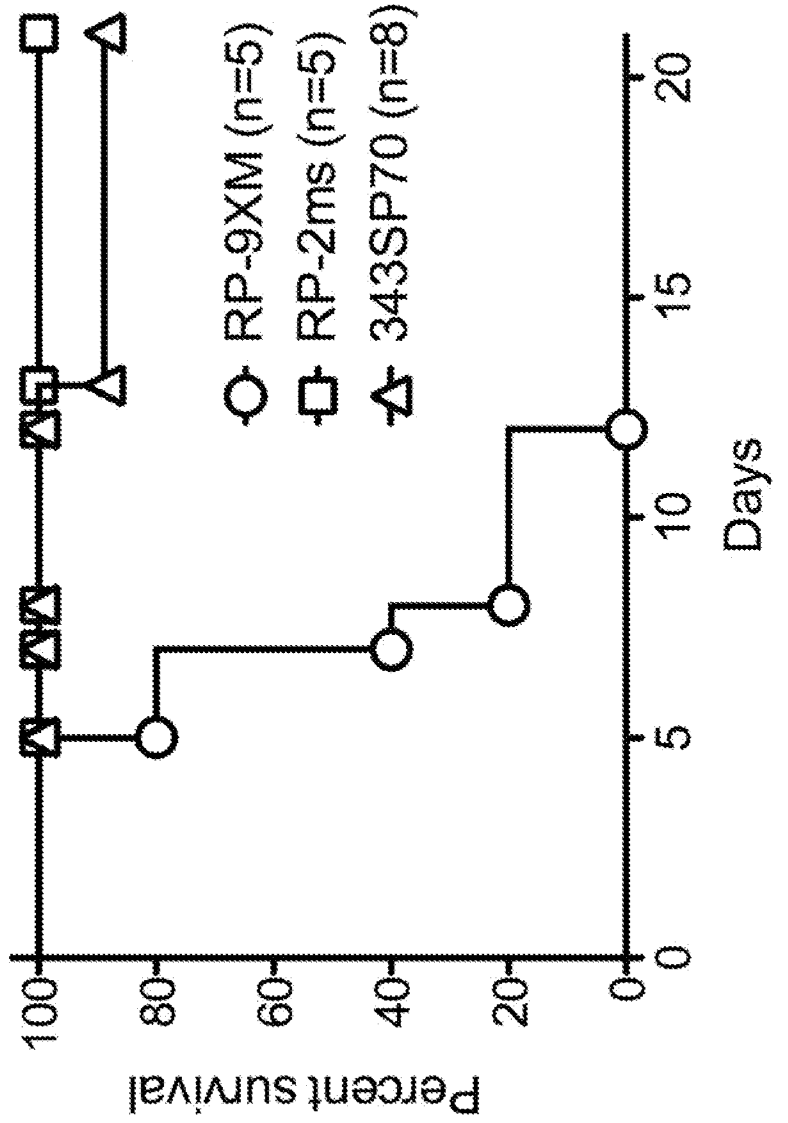
FIG. 9 depicts survival plotted as the percentage of survival animals versus time following injection of RP-9XM, RP-2 ms and 343SP70 (i.e., the recombinant JEV virus of this invention), respectively, in accordance with one embodiment of this invention.

In this example, survival test of animals inoculated with the recombinant JEV virus were performed. Mice, which were intracerebrally (i.c.) injected with 10 micro-liter PBS to break down blood-brain barrier (BBB), were intraperitoneally (i.p.) injected with $2\times10^5$ pfu (plaque formation unit) of the RP9-XM, $2\times10^5$ pfu of the RP-2 ms and $2\times10^5$ pfu of the recombinant JEV virus having an inserted EV71 SP70 epitope (i.e., 343SP70), respectively. Animals inoculated with RP9-XM died after 10 days, whereas over 90% animals inoculated with the infectious clone RP-2 ms or the recombinant JEV virus (i.e., 343SP70) remained healthy 21 days after injection (FIG. 9). The results demonstrate that the recombinant JEV virus of this invention is as attenuated as a vaccine strain RP-2 ms previously reported (Chen et al., Virology 223(1):79-88, 1996; Lin et al., Virus Res. 44(1):45-56, 1996; Liang et al., Vaccine 27(21):2746-2754, 2009).

Example 6

Inducing Specific Antibody Response in Mice Immunized with 343SP70

Figure 10:
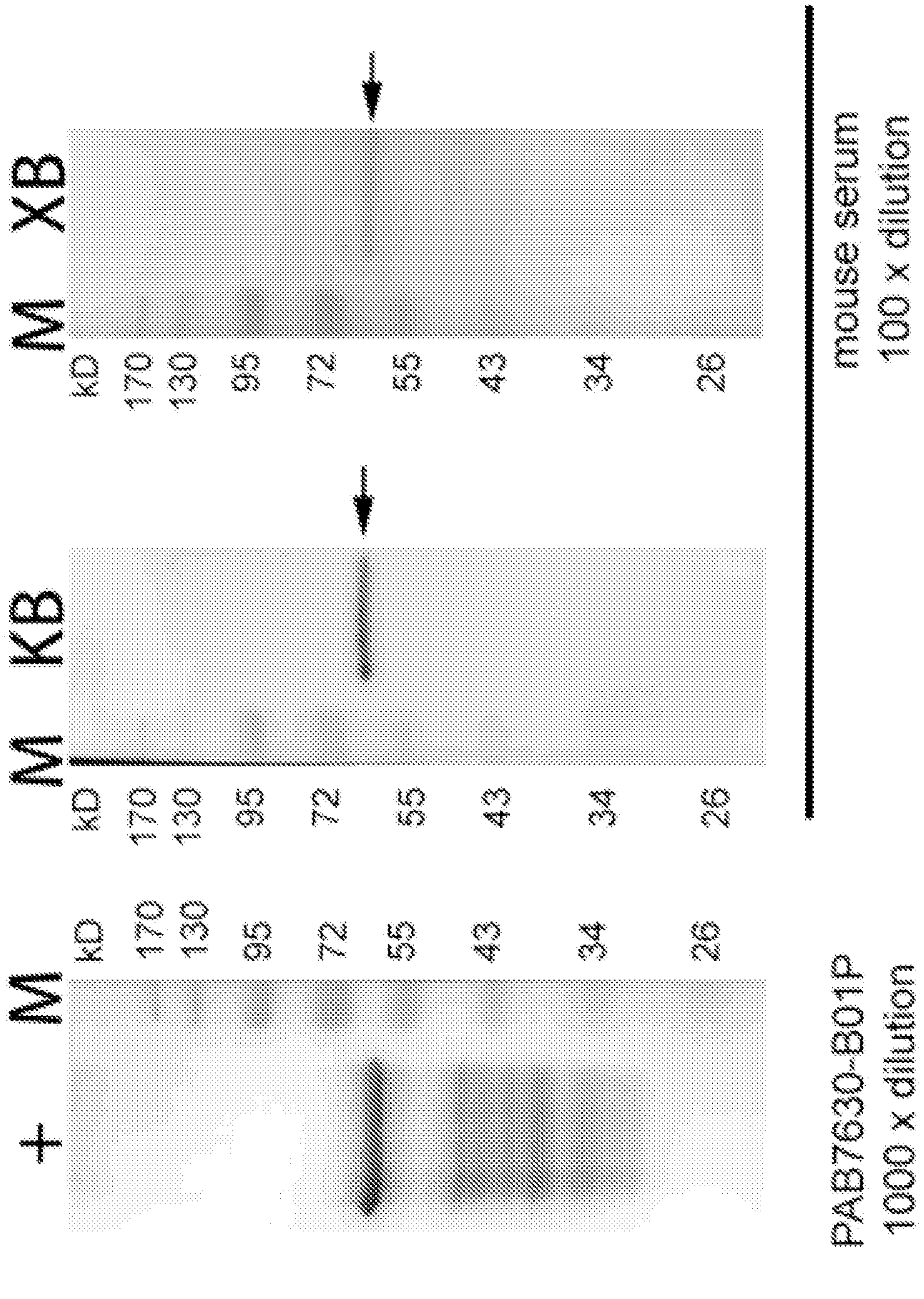
FIG. 10 depicts the responsiveness of mice immunized with 343SP70 to P3386 antigen analyzed by western blot in accordance with one embodiment of this invention.

In this example, whether JEV 343SP70-RP9 could induce the immunized mice a specific antibody response to recognize SP70 epitope was investigated. First, sera were individually collected from the mice infected with JEV 343SP70. Then, a recombinant EV71 VP1 protein (P3386, Abnova) was used as an antigen and immunoblot assay was performed to examine the sera. As a positive control, polyclonal antibody PAB7630-B01P (Abnova) against EV71 VP1 was employed. The results illustrated in FIG. 10 suggest that neutralizing epitope SP70 fused with JEV NS1 could indeed elicit a specific antibody response from the immunized mice.

Example 7

Producing Fusion Protein Comprising JEV NS1 and *Gaussia* Luciferase

In this example, *Gaussia* luciferase (Gluc), a secreted protein with 185 amino acids in length was used to investigate the possible capacity for an insertion to be engineered into NS1 C-terminus.

First, a J-R2A-Gluc replicon was obtained by inserting Gluc (185 amino acids) between the JEV $NS1_{343}$ and the tail $polypeptide_{344}$. However, this replicon did not replicate as efficiently as its parental J-R2A replicon.

Figure 11:
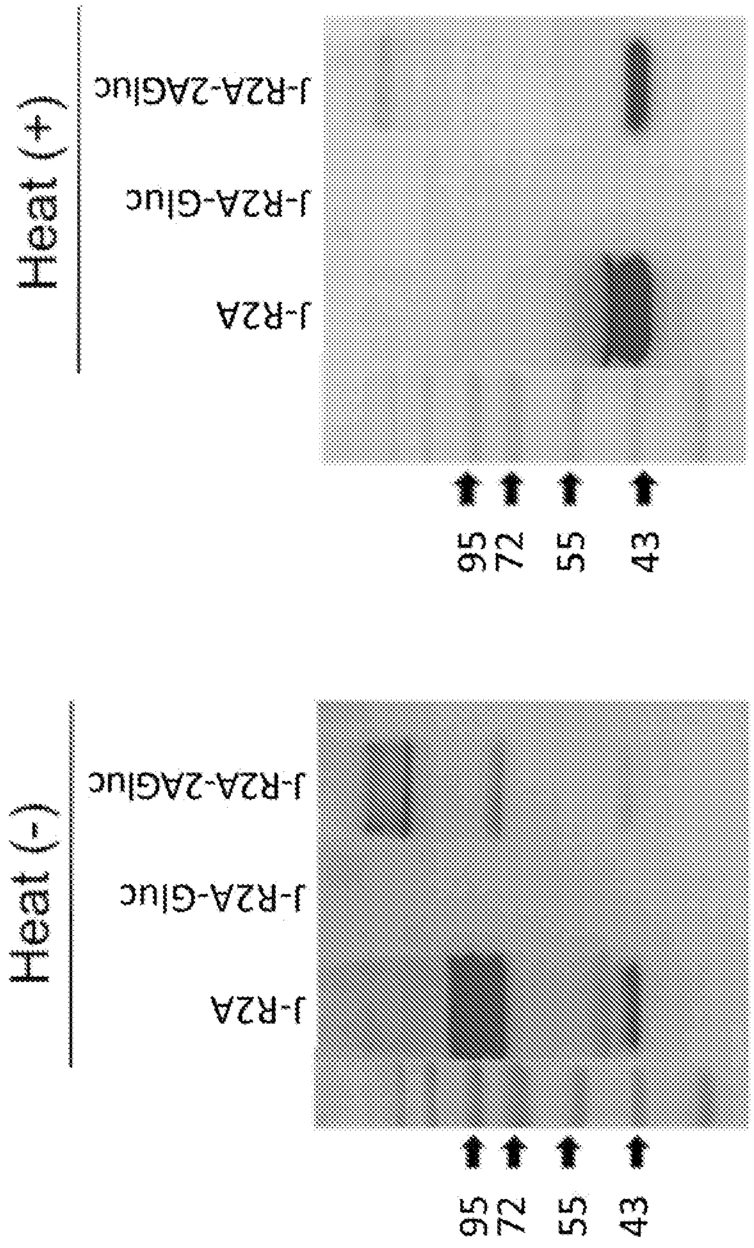
FIG. 11 depicts the secretion ability of the expressed fusion protein (i.e., JR2A-Glu and JR2A-2A-Glu) analyzed by western blot in accordance with one embodiment of this invention.

To solve this problem, an FMDV-2A peptide (NFDLLKLAGDVESNPGP, 17 amino acids) is fused in front of Gluc to obtain the J-R2A-2A-Gluc replicon. The J-R2A-2A-Gluc replicon, which comprises an exogenous polypeptide having 202 amino acids in length, appeared to replicate as well as the parental J-R2A replicon in the transfected BHK-21 cell by dual luciferase assay as described above (FIG. 11).

Without being bound by theory, it is believed that the translational cleavage functionality of the FMDV-2A peptide may properly separate JEV NS1 from the Gluc thereby facilitating the replication process. This result suggests that the inclusion of a protease segment in the exogenous polypeptide may improve the insertion capacity of the recombinant viral construct.

Example 8

Producing Fusion Protein Comprising JEV NS1 and EV71 VP1 Epitope

EV71 capsid protein VP1 is consisted of 297 amino acid residues. Therefore, an approach similar to that used in EXAMPLE 6 was adopted to design a replicon carrying EV71 VP1 epitope. Specifically, the exogenous polypeptide consisting of the FMDV 2A peptide (17 amino acids), the secretion signal peptide (MGVKVLFALICIAVAEAGL, 19 amino acids) derived from Gluc and the partial EV71 VP1 epitope (corresponding to amino acid residues from $145^{th}$ to $261^{st}$) were inserted between the JEV $NS1_{343}$ and the tail $polypeptide_{344}$ to produce a J-R2A-2A-Gss-VP1-C replicon. The total insertion size of this exogenous polypeptide was 153 amino acids in length. Dual luciferase assay indicated that J-R2A-2A-Gss-VP1-C replicon could replicate as efficiently as wild-type J-R2A replicon.

Example 9

Producing Fusion Proteins Comprising JEV NS1 and EV71 SP70 Epitope Inserted at Various Positions In this example, various insertion positions were investigated to elucidate whether these positions are capable of accommodating the insertion of exogenous polypeptides without affecting infectivity of the recombinant JEV.

Figure 12:
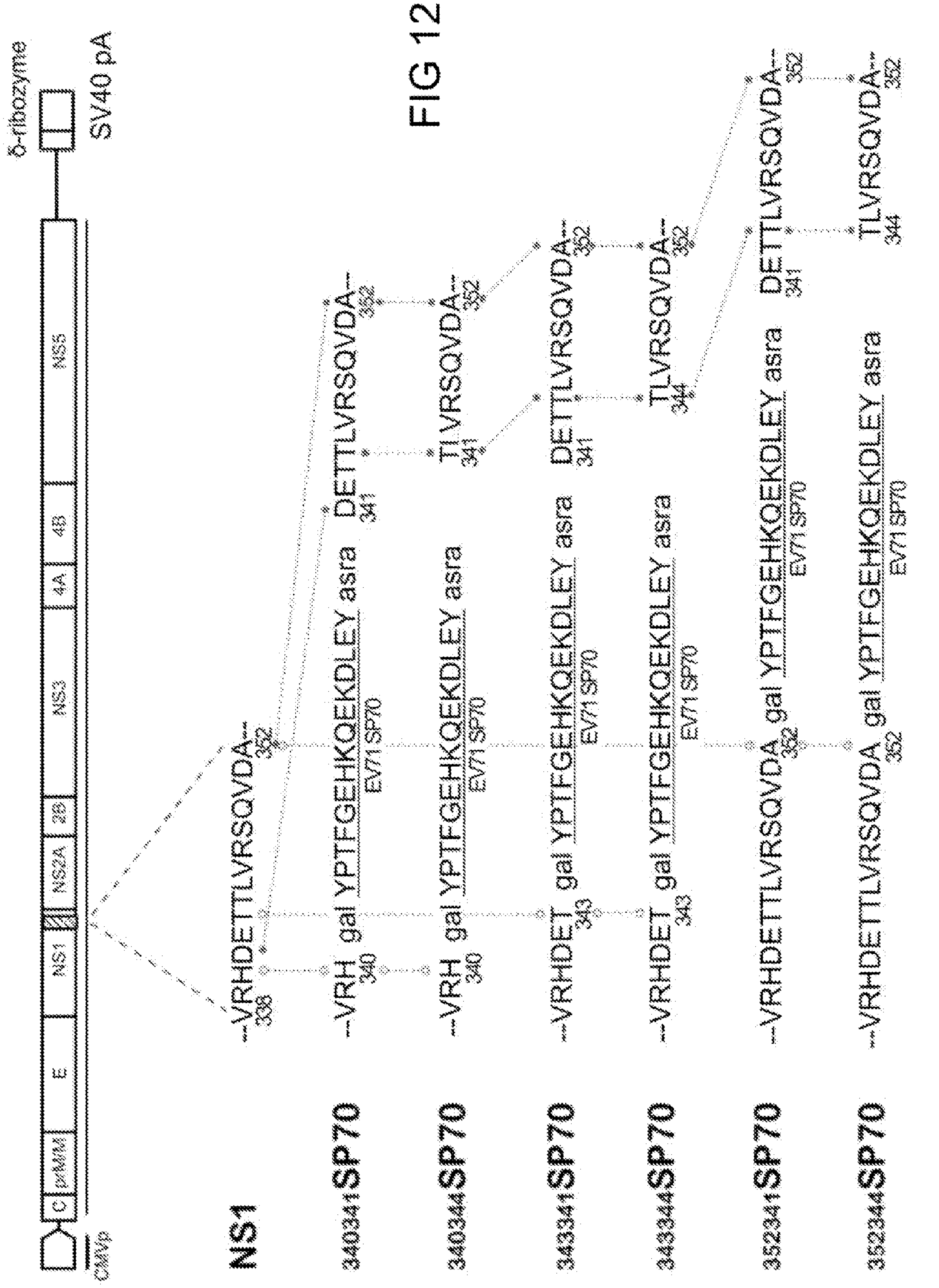
FIG. 12 summarizes various insertion positions for the EV71 SP70 antigen with linker (galYPTFGEHKQEKDLEYasra, SEQ ID NO: 11) inserted between various amino acid residues of JEV NS1 (SEQ ID NO. 16) according to embodiments of this invention (the fragment labeled NS1 illustrates a.a. 338-352 of SEQ ID NO: 16; $_{340341}$SP70 illustrates SEQ ID NO: 11 inserted between a.a. 340 and 341 of SEQ ID NO: 16; for $_{340344}$SP70 the insertion is between a.a. 340 and 344 with deletion of a.a. 341-343); for $_{343341}$SP70 the insertion is between a.a. 343 and 341 (with duplication of a.a. 341-343 after the insert); for $_{343344}$SP70 the insertion is between a.a. 343 and 344; for 352341SP70 the insertion is between a.a. 352 and a.a. 341 (with a duplication of a.a. 341-352); and for $_{352344}$SP70 the insertion is between a.a. 352 and a.a. 344 (with a duplication of a.a. 344-352)

Specifically, as illustrated in FIG. 12, six recombinant viral constructs $_{340341}$SP70, $_{340344}$SP70, $_{343341}$SP70, $_{343344}$SP70, $_{352341}$SP70, and $_{352344}$SP70 were constructed. These constructs were denoted in accordance with the amino acid sequences immediately before and after the EV71 SP70 antigen being inserted into the JEV NS1. For example, the cDNA clone of $_{340341}$SP70 denotes that the EV71 SP70 antigen was inserted between the JEV $NS1_{340}$ and the tail $polypeptide_{341}$ of the JEV NS1, whereas the cDNA clone of $_{352344}$SP70 denotes that the EV71 SP70 antigen was inserted between the JEV $NS1_{352}$ and the tail $polypeptide_{344}$.

Results from the constructed recombinant JEV vectors clearly indicate that the region surrounding the $343^{th}$ amino acid of JEV NS1 (e.g., the region including amino acids 340 to 352) is flexible for insertion of heterologous gene segment without significantly compromising the infectivity of the resultant recombinant JEV.

Figure 13:
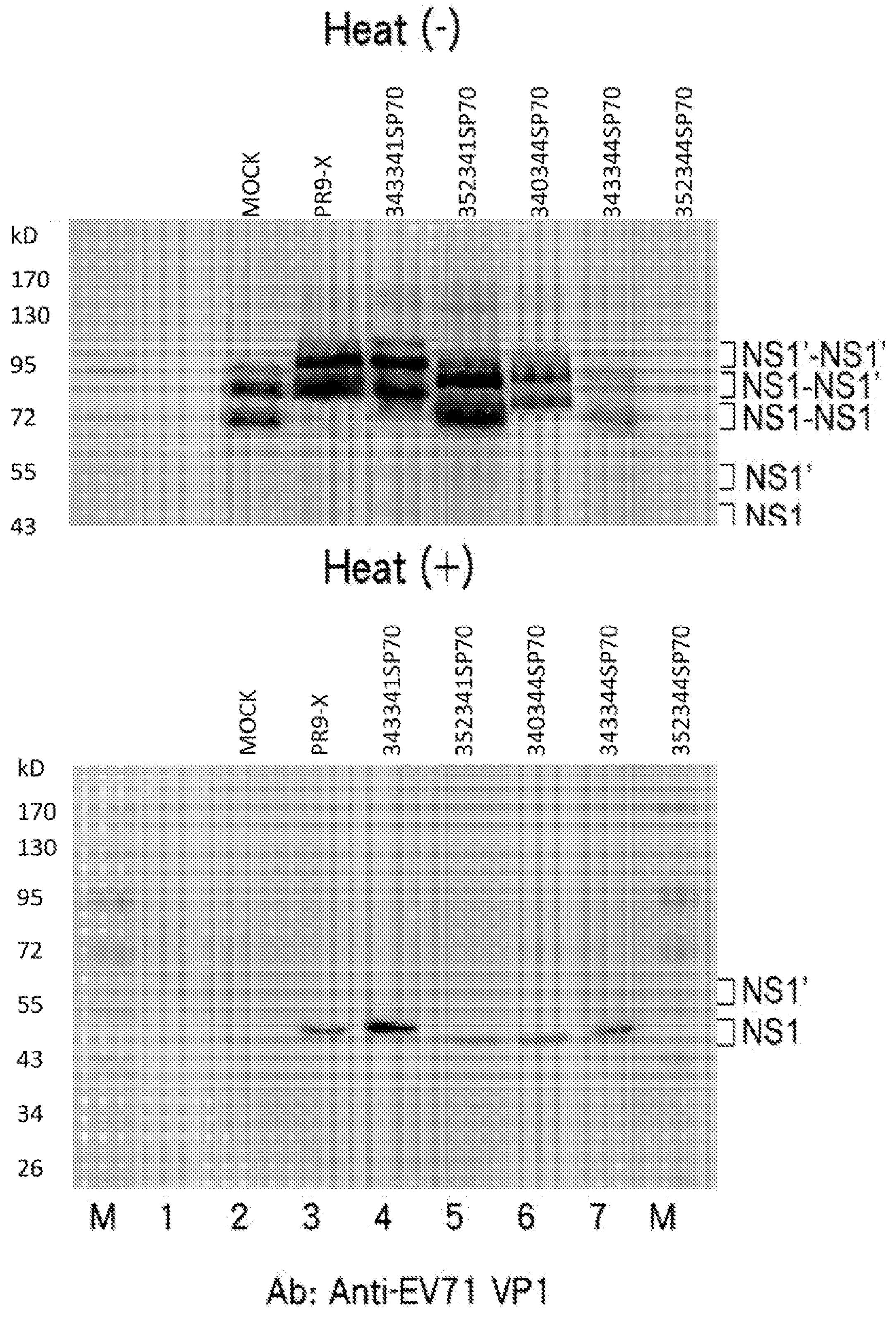
FIG. 13 depicts the secretion ability of the fusion proteins expressed by recombinant viral constructs of FIG. 12, which is analyzed by western blot in accordance with one embodiment of this invention.

The expression of NS1-SP70 fusion proteins were analyzed by Western blot using NS1 specific antibody or SP70 specific antiserum and the results are summarized in FIG. 13. Specifically, after 48-hour infection, culture medium was collected and concentrated as described above. Then, Western blot was performed using anti-serum J2-54 for JEV NS1 or anti-serum PAB7630-B01P (Abnova) for EV71 VP1. All the recombinant JEV tested could cause the infected cells to release NS1-SP70 fusion proteins into cultured medium, and more importantly, these fusion proteins could properly form dimer as the wild-type NS1 protein derived from RP-9 infection did. These results demonstrated JEV NS1 C-terminus is suitable for foreign peptide fusion and the fusion does not seem to interfere with the major functions of NS1 for JEV replication.

Example 10

Survival Plot of Animals Inoculated with $_{343341}$SP70 and $_{352341}$SP70 Recombinant JEV Viruses In this example, survival test of animals inoculated respectively with the recombinant $_{343341}$SP70 and $_{352341}$SP70 JEV viruses were investigated in accordance with similar procedures described above in Example 5.

Figure 14:
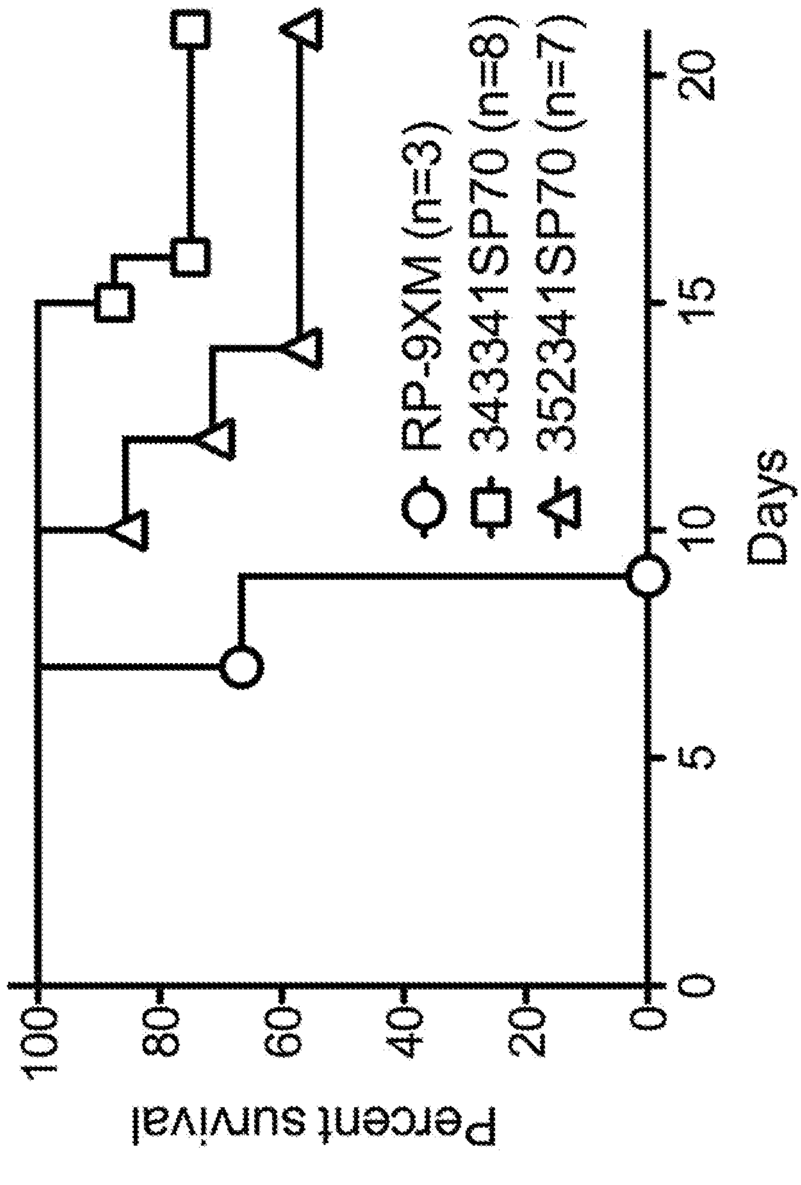
FIG. 14 depicts survival plotted as the percentage of survival animals versus time following injection of RP-9XM and recombinant JEV viruses of this invention (i.e., $_{343341}$SP70 and $_{352341}$SP70), respectively in accordance with one embodiment of this invention.

Animals inoculated with RP9-XM died within 10 days. By contrast, for animals inoculated respectively with the $_{343341}$SP70 and $_{352341}$SP70 recombinant JEV viruses, over 75% and 55% animals remained healthy 21 days after injection (FIG. 14). The results demonstrate that the recombinant JEV virus of this invention exhibited attenuated phenotype to the mice tested when compared with wild-type RP-9.

Example 11

Inducing Specific Antibody Response in Immunized Mice

Figure 15:
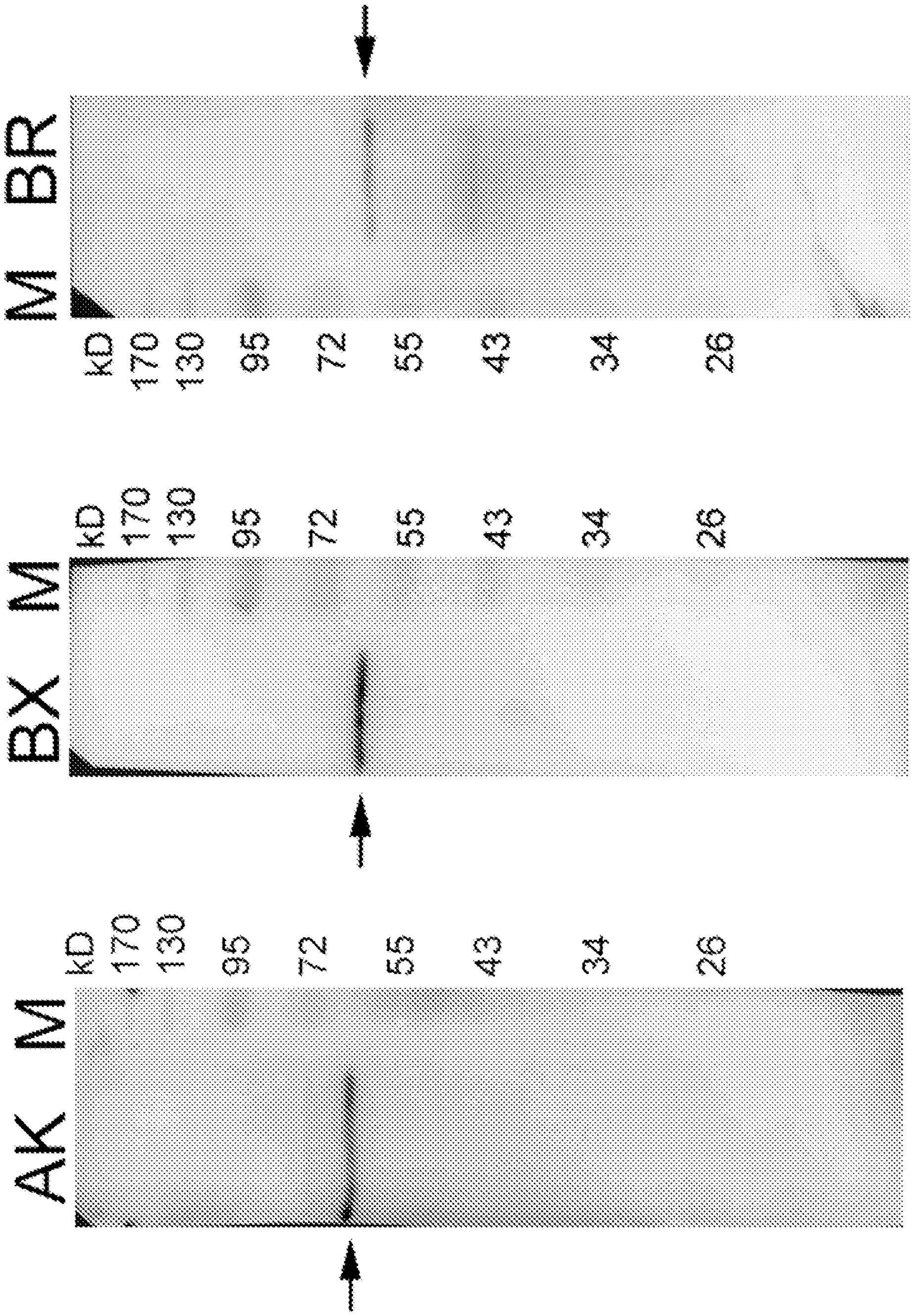
FIG. 15 depicts the responsiveness of mice immunized with $_{352341}$SP70 to P3386 antigen analyzed by western blot in accordance with one embodiment of this invention.

In this example, whether JEV $_{352341}$SP70 could induce the immunized mice a specific antibody response to recognize SP70 epitope was investigated in accordance with similar procedures described above in Example 6. The results illustrated in FIG. 15 suggest that the mice immunized with $_{352341}$SP70 could induce strong antibody response to EV71 VP1.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An isolated recombinant viral construct for expressing an exogenous polypeptide in a cell, comprising:

a Japanese encephalitis virus (JEV) replicon comprising a nucleic acid encoding a fusion protein comprising in sequence:

a JEV non-structural protein 1 (JEV NS1) segment comprising at least amino acid residues 1 to 340 of SEQ ID NO: 16;

the exogenous polypeptide having at least 6 amino acids; and a tail polypeptide comprising at least amino acid residues 344 to 352 of SEQ ID NO: 16, wherein the production of the fusion protein does not affect viral replication.

2. The isolated recombinant viral construct of claim 1, wherein the exogenous polypeptide comprises an immunogenic segment.

3. The isolated recombinant viral construct of claim 2, wherein the immunogenic segment is an Enterovirus 71 (EV71) SP70 antigen, an EV71 VP1 antigen or a portion thereof.

4. The isolated recombinant viral construct of claim 1, wherein the tail polypeptide comprises amino acid residues 341 to 352 of SEQ ID NO: 16.

5. The isolated recombinant viral construct of claim 1, wherein the JEV NS1 segment is amino acid residues 1 to 343 of SEQ ID NO: 16, and the tail polypeptide is amino acid residues 341 to 352 of SEQ ID NO: 16.

6. The isolated recombinant viral construct of claim 1, wherein the JEV NS1 segment is amino acid residues 1 to 343 of SEQ ID NO: 16, and the tail polypeptide is amino acid residues 344 to 352 of SEQ ID NO 16.

7. The isolated recombinant viral construct of claim 1, wherein the JEV NS1 segment is amino acid residues 1 to 352 of SEQ ID NO: 16, and the tail polypeptide is amino acid residues 341 to 352 of SEQ ID NO: 16.

8. The isolated recombinant viral construct of claim 1, wherein the JEV NS1 segment is amino acid residues 1 to 352 of SEQ ID NO: 16, and the tail polypeptide is amino acid residues 344 to 352 of SEQ ID NO: 16.

9. The isolated recombinant viral construct of claim 2, wherein the exogenous polypeptide further comprises a protease segment preceding the immunogenic segment, wherein the protease segment comprises a Foot-and-Mouth Disease virus 2A (FMDV-2A) peptide, and the exogenous polypeptide is at least 100 amino acids in length.

10. The isolated recombinant viral construct of claim 9, wherein the exogenous polypeptide further comprises a secretion-signal segment between the protease segment and the immunogenic segment, wherein the secretion-signal segment comprises a secretion signal peptide derived from *Gaussia* luciferase.

11. The isolated recombinant viral construct of claim 1, wherein the JEV replicon comprises a CMV promoter operably linked thereto such that the cell may express and subsequently secrete the fusion protein out of the cell.

12. The isolated recombinant viral construct of claim 1, wherein the cell is a BHK-21 cell, a C6/36 cell, or a Vero cell.

13. An isolated recombinant JEV particle, comprising a virion unit comprising an isolated recombinant viral construct of claim 1.

14. The isolated recombinant JEV particle of claim 13, wherein the exogenous polypeptide comprises an immunogenic segment, wherein the immunogenic segment is an Enterovirus 71 (EV71) SP70 antigen, an EV71 VP1 antigen or a portion thereof.

15. The isolated recombinant JEV particle of claim 13, wherein the exogenous polypeptide comprises an immunogenic segment and a protease segment preceding the immunogenic segment, wherein the protease segment comprises a Foot-and-Mouth Disease virus 2A (FMDV-2A) peptide, and the exogenous polypeptide is at least 100 amino acids in length.

16. A method of eliciting an immune response in a host, comprising administering the isolated recombinant JEV particle of claim 13 to the host, wherein said administering provides for expression of the exogenous polypeptide that results in induction of an immune response in the host to the exogenous polypeptide.

17. The method of claim 16, wherein the exogenous polypeptide comprises an immunogenic segment, wherein the immunogenic segment is an Enterovirus 71 (EV71) SP70 antigen, an EV71 VP1 antigen or a portion thereof.

18. The method of claim 16, wherein the exogenous polypeptide comprises an immunogenic segment and a protease segment preceding the immunogenic segment, wherein the protease segment comprises a Foot-and-Mouth Disease virus 2A (FMDV-2A) peptide, and the exogenous polypeptide is at least 100 amino acids in length.

19. The isolated recombinant JEV particle of claim 15, wherein the exogenous polypeptide further comprises a secretion-signal segment between the protease segment and the immunogenic segment, wherein the secretion-signal segment comprises a secretion signal peptide derived from *Gaussia* luciferase.

20. The method of claim 18, wherein the exogenous polypeptide further comprises a secretion-signal segment between the protease segment and the immunogenic segment, wherein the secretion-signal segment comprises a secretion signal peptide derived from *Gaussia* luciferase.

* * * * *

SEQUENCE LISTING

```
<160> NUMBER OF SEQ ID NOS: 16

<210> SEQ ID NO 1
<211> LENGTH: 34
<212> TYPE: DNA
<213> ORGANISM: Artificial Sequence
<220> FEATURE:
<223> OTHER INFORMATION: primer

<400> SEQUENCE: 1

gagggcccat ggtaccatgg gcgtcaacgc acga                                34


<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2

cagaccttcc atggaacac                                                 19


<210> SEQ ID NO 3
<211> LENGTH: 42
<212> TYPE: DNA
<213> ORGANISM: Artificial Sequence
<220> FEATURE:
<223> OTHER INFORMATION: primer
```

<400> SEQUENCE: 3
cataaacttt cgaagtcata ccggttacta ccctcttcac tc 42

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
agaagtttat ctgtgtgaac ttctt 25

<210> SEQ ID NO 5
<211> LENGTH: 37
<212> TYPE: DNA
<213> ORGANISM: Artificial Sequence
<220> FEATURE:
<223> OTHER INFORMATION: primer

<400> SEQUENCE: 5
ctggtaccgg cggccgcttg ttcatttttg agaactc 37

<210> SEQ ID NO 6
<211> LENGTH: 44
<212> TYPE: DNA
<213> ORGANISM: Artificial Sequence
<220> FEATURE:
<223> OTHER INFORMATION: primer

<400> SEQUENCE: 6
gctagcggcc gccaacttcg acctcctcaa gttggcggga gacg 44

<210> SEQ ID NO 7
<211> LENGTH: 45
<212> TYPE: DNA
<213> ORGANISM: Artificial Sequence
<220> FEATURE:
<223> OTHER INFORMATION: primer

<400> SEQUENCE: 7
ctggtacccg gcccagggtt ggactcaacg tctcccgcca acttg 45

<210> SEQ ID NO 8
<211> LENGTH: 42
<212> TYPE: DNA
<213> ORGANISM: Artificial Sequence
<220> FEATURE:
<223> OTHER INFORMATION: primer

<400> SEQUENCE: 8
tcctaggggc tgcctttttc cagttagcct cagtagatct gc 42

<210> SEQ ID NO 9
<211> LENGTH: 46
<212> TYPE: DNA
<213> ORGANISM: Artificial Sequence
<220> FEATURE:
<223> OTHER INFORMATION: primer

<400> SEQUENCE: 9
tgaacctgaa acataaaatg aatgcagttg ttgttgttaa cttgtt 46

<210> SEQ ID NO 10

<211> LENGTH: 15
<212> TYPE: PRT
<213> ORGANISM: Enterovirus
<220> FEATURE:
<223> OTHER INFORMATION: EV71 SP70

<400> SEQUENCE: 10

```
Tyr Pro Thr Phe Gly Glu His Lys Gln Glu Lys Asp Leu Glu Tyr
1               5                   10                  15
```

<210> SEQ ID NO 11
<211> LENGTH: 22
<212> TYPE: PRT
<213> ORGANISM: Artificial Sequence
<220> FEATURE:
<223> OTHER INFORMATION: EV71 SP70 with linker

<400> SEQUENCE: 11

```
Gly Ala Leu Tyr Pro Thr Phe Gly Glu His Lys Gln Glu Lys Asp Leu
1               5                   10                  15

Glu Tyr Ala Ser Arg Ala
            20
```

<210> SEQ ID NO 12
<211> LENGTH: 39
<212> TYPE: PRT
<213> ORGANISM: Artificial Sequence
<220> FEATURE:
<223> OTHER INFORMATION: 2XSP70

<400> SEQUENCE: 12

```
Gly Ala Leu Tyr Pro Thr Phe Gly Glu His Lys Gln Glu Lys Asp Leu
1               5                   10                  15

Glu Tyr Ala Leu Tyr Pro Thr Phe Gly Glu His Lys Gln Glu Lys Asp
            20                  25                  30

Leu Glu Tyr Ala Ser Arg Ala
        35
```

<210> SEQ ID NO 13
<211> LENGTH: 56
<212> TYPE: PRT
<213> ORGANISM: Artificial Sequence
<220> FEATURE:
<223> OTHER INFORMATION: 3XSP70

<400> SEQUENCE: 13

```
Gly Ala Leu Tyr Pro Thr Phe Gly Glu His Lys Gln Glu Lys Asp Leu
1               5                   10                  15

Glu Tyr Ala Leu Tyr Pro Thr Phe Gly Glu His Lys Gln Glu Lys Asp
            20                  25                  30

Leu Glu Tyr Ala Leu Tyr Pro Thr Phe Gly Glu His Lys Gln Glu Lys
        35                  40                  45

Asp Leu Glu Tyr Ala Ser Arg Ala
    50                  55
```

<210> SEQ ID NO 14
<211> LENGTH: 73
<212> TYPE: PRT
<213> ORGANISM: Artificial Sequence
<220> FEATURE:
<223> OTHER INFORMATION: 4XSP70

<400> SEQUENCE: 14

```
Gly Ala Leu Tyr Pro Thr Phe Gly Glu His Lys Gln Glu Lys Asp Leu
```

-continued

```
1               5                   10                  15

Glu Tyr Ala Leu Tyr Pro Thr Phe Gly Glu His Lys Gln Glu Lys Asp
            20                  25                  30

Leu Glu Tyr Ala Leu Tyr Pro Thr Phe Gly Glu His Lys Gln Glu Lys
        35                  40                  45

Asp Leu Glu Tyr Ala Leu Tyr Pro Thr Phe Gly Glu His Lys Gln Glu
    50                  55                  60

Lys Asp Leu Glu Tyr Ala Ser Arg Ala
65                  70
```

<210> SEQ ID NO 15
<211> LENGTH: 10976
<212> TYPE: DNA
<213> ORGANISM: Japanese encephalitis virus
<220> FEATURE:
<223> OTHER INFORMATION: Japanese encephalitis virus polyprotein cDNA

<400> SEQUENCE: 15

```
agaagtttat ctgtgtgaac ttcttggctt agtatcgttg agaagaatcg agagattagt     60

gcagtttaaa cagtttttta gaacggaaga taaccatgac taaaaaacca ggagggcccg    120

gtaaaaaccg ggctatcaat atgctgaaac gcggcctacc ccgcgtattc ccactagtgg    180

gagtgaagag ggtagtaatg agcttgttgg acggcagagg gccagtacgt ttcgtgctgg    240

ctcttatcac gttcttcaag tttacagcat tagccccgac caaggcgctt ctaggccgat    300

ggaaagcagt ggaaaagagt gtagcaatga aacatctcac tagtttcaaa cgagaacttg    360

gaacactcat tgacgccgtg aacaagcggg gcagaaagcg aaacaaaaga ggaggaaatg    420

aaggctcaat catgtggctc gcgagcttgg cagttgtcat agcttgtgca ggagccatga    480

agttgtcaaa tttccagggg aagcttttga tgaccattaa caacacggac attgcagacg    540

ttatcgtgat tcccacctca aaaggagaga acagatgctg ggtccgggca atcgacgtcg    600

gctacttgtg tgaggacact atcacgtacg aatgtcctaa gcttaccatg ggcaatgatc    660

cagaggatgt ggattgctgg tgtgacaacc aagaagtcta cgtccaatat ggacggtgca    720

cgcggaccag acattccaag cgaacgagga gatccgtgtc ggtccaaaca catggggaga    780

gttcactagt gaataaaaaa gaggcttggc tggattcaac gaaagccaca cgatatctca    840

tgaaaactga gaactggatc ataaggaatc ctggctatgc tttcctggcg gcggtacttg    900

gctggatgct tggcagtaac aacggtcaac gcgtggtatt caccatcctc ctgctgctgg    960

ttgctccggc ttacagtttt aattgtctgg gaatgggcaa tcgtgacttc atagaaggag   1020

ccagtggagc cacttgggtg gacttggtgc tagaaggaga tagctgcttg acaattatgg   1080

caaacgacaa accaacattg gacgtccgca tgatcaacat cgaagctagc caacttgctg   1140

aggtcagaag ttactgttat catgcttcag tcactgacat ctcgacggtg gctcggtgcc   1200

ccacgactgg agaagcccac aacgagaagc gagctgatag tagctatgtg tgcaaacaag   1260

gcttcactga tcgtgggtgg ggcaacggat gtggactttt cgggaaggga agcattgaca   1320

catgtgcaaa attctcctgc accagtaaag cgattgggag aacaatccag ccagaaaaca   1380

tcaaatacga agttggcatt tttgtgcatg gaaccaccac ttcggaaaac catgggaatt   1440

attcagcgca agttggggcg tcccaggcgg caaagtttac agtaacaccc aatgctcctt   1500

cgataaccct caaacttggt gactacggag aagtcacact ggactgtgag ccaaggagtg   1560

gactgaacac tgaagcgttt tacgtcatga ccgtggggtc aaagtcattt ctggtccata   1620

gggaatggtt tcatgacctc gctctcccct ggacgtcccc ttcgagcaca gcgtggagaa   1680
```

-continued

```
acagagaact cctcatggag tttgaagagg cgcacgccac aaaacagtcc gttgttgctc   1740
ttgggtcaca ggaaggaggc ctccatcagg cgttggcagg agccatcgtg gtggagtact   1800
caagctcagt gaagttaaca tcaggccacc tgaaatgtag gctgaaaatg gacaaactgg   1860
ctctgaaagg cacaacctat ggcatgtgca cagaaaaatt ctcgttcgca aaaaatccgg   1920
cggacactgg tcacggaaca gttgtcatcg aactctccta ctctgggagt gatggcccct   1980
gcaaaattcc gattgtctcc gttgcgagcc tcaatgacat gacccccgtt gggcggctgg   2040
tgacagtgaa ccccttcgtc gcgacttcca gtgccaattc aaaggtgctg gtcgagatgg   2100
aacccccctt cggagactcc tacatcgtga ttggaagggg agacaagcag atcaaccacc   2160
attggcacaa agctggaagc acgctgggca aagccttttc aacaactttg aagggagctc   2220
agagactggc agcgttgggt gacacagcct gggactttgg ctccattgga ggggtcttca   2280
actccatagg aaaagccgtt caccaagtgt ttggtggtgc cttcagaaca ctctttgggg   2340
gaatgtcttg gatcacacaa gggctaatgg gtgccctact actctggatg ggcgtcaacg   2400
cacgagaccg atcaattgct ttggccttct tagccacagg aggtgtgctc gtgttcttag   2460
cgaccaatgt gcatgctgac actggatgtg ccattgacat cacaagaaaa gagatgaggt   2520
gtggaagtgg catcttcgtg cacaacgacg tggaagcctg ggtggatagg tataaatatt   2580
tgccagaaac gcccagatcc ctagcgaaga tcgtccacaa agcgcacaag gaaggcgtgt   2640
gcggagtcag atctgtcact agactggagc atcaaatgtg ggaagccgta cgggatgaat   2700
tgaacgtcct gctcaaagag aatgcagtgg acctcagtgt ggttgtgaac aagcccgtgg   2760
ggagatatcg ctcagcccct aaacgcctat ccatgacgca agagaagttt gaaatgggct   2820
ggaaagcatg ggaaaaaagc attctctttg ccccggaatt ggctaactcc acatttgtcg   2880
tagatggacc tgagacaaag gaatgccctg atgagcacag agcttggaac agcatgcaaa   2940
tcgaagactt cggctttggc atcacatcaa cccgtgtgtg gctgaagatt agagaggaga   3000
gcactgacga gtgtgatgga gcgatcatag gtacggctgt caaaggacat gtggcagtcc   3060
atagtgactt gtcgtactgg attgagagtc gctacaacga cacatggaaa cttgagaggg   3120
cagtctttgg agaggttaaa tcttgcactt ggccagagac acacaccccta tggggagatg   3180
gtgttgagga aagtgaactc atcattccgc ataccatagc cggaccaaaa agcaagcaca   3240
atcggaggga agggtataag acacaaaacc agggaccttg ggacgagaat ggcatagtct   3300
tggactttga ctattgccca gggacaaaag tcaccattac agaggattgt ggcaagagag   3360
gcccttcggt cagaaccact actgacagtg gaaagttgat cactgactgg tgctgtcgca   3420
gttgctccct tccgccccta cgattccgga cagaaaatgg ctgctggtac ggaatggaaa   3480
tcagacctgt taggcatgat gaaacaacac tcgtcagatc acaggttgat gcttttaatg   3540
gtgaaatggt tgaccctttt cagctgggcc ttctggtgat gtttctggcc acccaggagg   3600
tccttcgcaa gaggtggacg gccagattga ccattcctgc ggttttggga gccttacttg   3660
tgctgatgct tgggggcatc acttacactg atttggcgag gtatgtggtg ctagtcgctg   3720
ctgctttcgc agaggccaac agtggaggag acgtcctgca ccttgctttg attgccgttt   3780
ttaagatcca accagcattt ttagtgatga acatgcttag cacgagatgg acgaaccaag   3840
aaaacgtggt tctggtccta ggggctgcct ttttccaatt ggcctcagta gatctgcaaa   3900
taggagttca cggaatcctg aatgccgccg ctatagcatg gatgattgtc cgggcgatca   3960
ccttccccac aacctcctcc gtcaccatgc cagtcttagc gcttctaacc ccgggaatga   4020
```

-continued

```
gggctctata cctagatact tacagaatca tcctcctcgt catagggatt tgctctctgc   4080
tgcaagagag gaaaaagacc atggcaaaaa agaaaggagc tgtactcttg ggcttagcgc   4140
tcacatccac tggatggttt tcgcccacca ctatagctgc cggactaatg gtctgcaacc   4200
caaacaagaa gagagggtgg ccagctactg agtttttgtc ggcagttgga ttgatgtttg   4260
ccatcgtagg tggtttggca gagttggata ttgaatccat gtcaataccc ttcatgctgg   4320
caggtctcat ggcagtgtcc tacgtggtgt caggaaaagc aacagatatg tggcttgaac   4380
gggccgccga catcagctgg gagatggatg ctgcaatcac aggaagcagt cggaggctgg   4440
atgtgaagct ggatgaagac ggagattttc acttgattga tgatcccggt gttccatgga   4500
aggtctgggt cctgcgcatg tcttgcattg gcttagccgc cctcacgcct tgggccattg   4560
ttcccgccgc ttttggttat tggctcactt taaaaacaac aaaaagagga ggcgtgtttt   4620
gggacacgcc atccccaaaa ccttgctcaa aaggagacac cactacagga gtttaccgca   4680
ttatggctag agggattctt ggcacttacc aggccggcgt cggagtcatg tacgagaatg   4740
ttttccacac actatggcac acaactagag gagcagccat tatgagtgga gaaggaaaat   4800
tgacgccata ctggggtagt gtgaaagaag accgcatagc ttacggaggc ccatggaggt   4860
ttgatcgaaa atggaatgga acagatgacg tgcaagtgat cgtggtagaa ccggggaagg   4920
ctgcagtaaa catccagaca aaaccagggg tgtttcggac tcccttcggg gaggttgggg   4980
ctgttagtct ggattacccg cgaggaacat ccggctcacc cattctggat tccaatggag   5040
acatcatagg cctgtacggc aatggagttg agcttggcga tggttcatac gtcagcgcca   5100
tcgtgcaggg tgaccgtcag gaggaaccag tcccagaagc ttacacccca aacatgttga   5160
gaaagagaca gatgactgta ctagatttgc accctggttc agggaaaacc aggaaaattc   5220
tgccacaaat aattaaggac gctatccagc agcgcctaaa aacagctgtg ttggcaccga   5280
cgcgggtggt agcagcagaa atggcagaag ctttgagagg gctcccagta cgatatcaaa   5340
cttcagcagt gcagagagag caccaaggga atgaaatagt ggatgtgatg tgccacgcca   5400
ctctgaccca tagactgatg tcaccgaaca gagtgcccaa ctacaaccta tttgtcatgg   5460
atgaagctca tttcaccgac ccagccagta tagctgcacg aggatacatt gctaccaagg   5520
tggaattagg ggaggcagca gccatcttta tgacagcgac cccgcctgga accacggatc   5580
cttttcctga ctcaaatgcc ccaatccatg atttgcaaga tgagatacca gacagggcgt   5640
ggagcagtgg atacgaatgg atcacagaat atgcgggcaa aaccgtgtgg tttgtggcaa   5700
gcgtaaaaat ggggaatgag attgcaatgt gcctccaaag agcggggaaa aaggtcatcc   5760
aactcaaccg caagtcctat gacacagaat acccaaaatg taagaatgga gactgggatt   5820
ttgtcatcac caccgacatc tctgaaatgg gggccaactt cggtgcgagc agggtcatcg   5880
actgtagaaa gagcgtgaag cctaccatct tagaagaggg agaaggcaga gtcatcctcg   5940
gaaacccatc ccccataacc agtgcaagcg cagctcaacg gaggggcagg gtaggcagaa   6000
accccaacca ggttggagat gaataccact atgggggggc caccagtgaa gatgacagta   6060
atctagccca ttggacagag gcaaagatca tgttagacaa catacacatg cccaatggac   6120
tggtggccca gctctatgga ccagagaggg aaaaggcctt cacaatggat ggcgaatacc   6180
gtctcagagg tgaagaaaag aaaaacttct tagagctgct taggacggct gacctcccgg   6240
tgtggctggc ctacaaggtg gcgtccaatg gcattcagta caccgacaga aagtggtgtt   6300
```

-continued

```
ttgatgggcc gcgcacgaat gccatactgg aggacaacac cgaggtagag atagtcaccc   6360
ggatgggtga gaggaaaatc ctcaagccga gatggcttga tgcaagagtt tatgcagatc   6420
accaagccct caagtggttc aaagacttcg cagcagggaa gagatcagcc gttagcttca   6480
tagaggtgct cggtcgtatg cctgagcatt tcatgggaaa gacgcgggaa gctttagaca   6540
ccatgtactt ggttgcaacg gctgagaaag gtgggaaagc acaccgaatg gctctcgaag   6600
agctgccaga tgcactggaa accattacac ttattgttgc tatcactgtg atgacaggag   6660
gattctttct actcatgatg cagcggaagg gtatagggaa gatgggtctt ggagctctag   6720
tgctcacgct agctaccttc ttcctgtggg cggcagaggt tcctggaacc aaaatagcag   6780
ggaccctgct gatcgccctg ctgcttatgg tggttctcat cccagaaccg gaaaaacaga   6840
ggtcacagac agataaccaa ctggcggtgt ttctcatctg tgtcttgacc gtggttggag   6900
tggtggcagc aaacgagtac ggaatgctag aaaaaaccaa agcagacctc aagagcatgt   6960
ttggcggaaa gacgcaggca tcaggactga ctggattgcc aagcatggca ttggacctgc   7020
gtccagccac agcttgggca ctgtatgggg ggagcacagt cgtgctaacc cctcttctga   7080
agcacctgat cacgtcggaa tacgtcacca catcgctagc ctcaattaac tcacaagctg   7140
gctcattatt tgtcttgcca cgaggcgtgc cttctaccga cctagacttg accgttggcc   7200
tcgtcttcct tggctgttgg ggtcaaatca ccctcacaac gtttttgaca gccatggttc   7260
tggcgacact tcactatggg tacatgctcc ctggatggca agcagaagca ctcagagctg   7320
cccagagaag gacagcggct ggaataatga agaatgccgt tgttgacgga atggtcgcca   7380
ctgatgtgcc tgaactggaa aggaccactc ctctgatgca aaagaaagtc ggacaggtgc   7440
tcctcatagg ggtaagcgtg gcagcgttcc tcgtcaaccc caatgtcacc actgtgagag   7500
aagcaggggt gttggtgacg gcgcgtacgc tcactttgtg ggacaatgga gccagtgccg   7560
tttggaattc caccactgcc acgggactct gccatgtaat gcgaggtagc tacctgcgcg   7620
gaggctccat tgcttggact ctcatcaaga acgctgacaa gccctccttg aaaaggggaa   7680
ggcctggggg caggacgcta ggggagcagt ggaaggaaaa actaaatgcc atgagcagag   7740
aagagttttt taaataccgg agagaggcca taatcgaggt ggaccgcact gaagcacgca   7800
gggctagacg tgaaaataac atagtgggag gacatccggt ttcgcgaggc tcagcaaaac   7860
tccgttggct cgtggagaaa ggatttgtct cgccaatagg aaaagtcatt gatctagggt   7920
gtgggcgtgg aggatggagc tactacgcag caaccctgaa gaaggtccag gaagtcagag   7980
gatacacgaa aggtggggcg ggacatgaag aaccgatgct catgcagagc tacggctgga   8040
acctggtctc cctgaagagt ggagtggacg tgttttacaa accttcagag cccagtgaca   8100
ctctgttctg cgacataggg gaatcctccc caagtccaga agtagaagaa caacgcacat   8160
tacgcgtcct agagatgaca tctgactggt tgcaccgagg acctagagag ttctgcataa   8220
aagttctttg cccctacatg cccaaggtca tagaaaaaat ggaagttctg cagcgccgct   8280
tcggaggtgg gctagtgcgt ctccccctgt cccgcaactc caatcacgag atgtattggg   8340
ttagtggagc cgctggcaat gtggtgcacg ctgtgaacat gaccagccag gtactactgg   8400
ggcgaatgga tcgcacagtg tggagagggc caaagtatga ggaagatgtc aacctaggga   8460
gcggaacaag agccgtggga aagggagaag tccatagcaa tcaggagaaa atcaagaaga   8520
gaatccagaa gcttaaagaa gaattcgcca caacgtggca caaagaccct gagcatccat   8580
```

accgcacttg gacataccac ggaagctatg aagtgaaggc tactggctca gctagctctc 8640
tcgtcaacgg agtggtgaag ctcatgagca aaccttggga cgccattgcc aacgtcacca 8700
ccatggccat gactgacacc accccgtttg gacagcaaag agttttcaag gagaaagttg 8760
acacgaaggc tcctgagcca ccagctggag ccaaggaagt gctcaacgag accaccaact 8820
ggctgtgggc ctacttgtca cgggaaaaaa gacccccgctt gtgcaccaag gaagaattca 8880
taaagaaagt caatagcaac gcggctcttg gagcagtgtt cgctgaacag aatcaatgga 8940
gcacggcgcg tgaggctgtg gatgacccgc ggttttggga gatggttgat gaagagaggg 9000
aaaaccatct gcgaggagag tgtcacacat gtatctacaa catgatggga aaaagagaga 9060
agaagcctgg agagtttgga aaagctaaag gaagcagggc catttggttc atgtggcttg 9120
gagcacggta tctagagttt gaagctttgg ggttcctgaa tgaagaccat tggctgagcc 9180
gagagaattc aggaggtgga gtggaaggct caggcgtcca aaagctggga tacatcctcc 9240
gtgacatagc aggaaagcaa ggagggaaaa tgtatgctga tgacaccgcc gggtgggaca 9300
ctagaattac cagaactgat ttagaaaatg aagctaaggt gctggagctt ctagatggtg 9360
aacaccgcat gctcgcccga gccataattg aattgactta caggcacaaa gtggtcaagg 9420
tcatgagacc tgcagcagaa ggaaagaccg tgatggacgt gatatcaaga gaagatcaaa 9480
gggggagtgg acaggtggtc acttatgctc ttaacacttt cacgaacatc gctgtccagc 9540
tcgtcaggct gatggaggct gagggggtca ttggaccaca acacttggaa cagctaccta 9600
gaaaaaacaa gatagctgtc aggacctggc tctttgagaa tggagaggag agagtgacca 9660
ggatggcgat cagcggagac gactgtgtcg tcaagccgct ggacgacaga ttcgccacgg 9720
ccctccactt cctcaacgca atgtcaaagg tcagaaagga catccaggaa tggaagcctt 9780
cgcatggttg gcacgactgg cagcaagttc ccttctgctc taaccatttt caggagattg 9840
tgatgaaaga tggaaggagt atcgttgtcc cgtgcagagg acaggatgag ctgataggca 9900
gggctcgcat ctccccagga gctggatgga atgtgaagga cacagcttgt ctggccaaag 9960
catatgcaca gatgtggcta ctcctatact tccatcgtag gtacttgcgt ctcatggcaa 10020
atgcaatttg ctcagcagtg ccagtggatt gggtgcccac gggcaggaca tcctggtcga 10080
tacactcgaa aggagagtgg atgaccacag aagacatgct gcaggtctgg aacagagtct 10140
ggattgaaga aaatgaatgg atgatggaca agactccaat cacaagctgg acagacgttc 10200
cgtacgtggg aaagcgtgag gacatctggt gtggtagcct catcggaacg cgatccagag 10260
caacctgggc tgagaacatc tacgcggcga taaaccaggt tagagctgtc attgggaaag 10320
aaaattatgt tgactacatg acctcactca ggagatacga agacgtcttg atccaggaag 10380
acagggtcat ctagtgtgat ttaaggtaga aaagtagact atgtaaataa tgtaaatgag 10440
aaaatgcatg catatggagt caggccagca aaagctgcca ccggatactg ggtagacggt 10500
gctgcctgcg tctcagtccc aggaggactg ggttaacaaa tctgacaata gaaagtgaga 10560
aagccctcag aaccgtctcg gaagcaggtc cctgctcact ggaagttgaa ggaccaacgt 10620
caggccacaa atttgtgcca ctccgctggg gagtgcggcc tgcgcagccc caggaggact 10680
gggttaccaa agccgttgag cccccacggc ccaagcctcg tctaggatgc aatagacgag 10740
gtgtaaggac tagaggttag aggagacccc gtggaaacaa caacatgcgg cccaagcccc 10800
ctcgaagctg tagaggaggt ggaaggacta gaggttagag gagaccccgc atttgcatca 10860
aacagcatat tgacacctgg gaatagactg ggagatcttc tgctctatct caacatcagc 10920

-continued tactaggcac agagcgccga agtatgtagc tggtggtgag gaagaacaca ggatct 10976

<210> SEQ ID NO 16
<211> LENGTH: 352
<212> TYPE: PRT
<213> ORGANISM: Japanese encephalitis virus
<220> FEATURE:
<223> OTHER INFORMATION: NS1

<400> SEQUENCE: 16

Asp Thr Gly Cys Ala Ile Asp Ile Thr Arg Lys Glu Met Arg Cys Gly
1 5 10 15

Ser Gly Ile Phe Val His Asn Asp Val Glu Ala Trp Val Asp Arg Tyr
20 25 30

Lys Tyr Leu Pro Glu Thr Pro Arg Ser Leu Ala Lys Ile Val His Lys
35 40 45

Ala His Lys Glu Gly Val Cys Gly Val Arg Ser Val Thr Arg Leu Glu
50 55 60

His Gln Met Trp Glu Ala Val Arg Asp Glu Leu Asn Val Leu Leu Lys
65 70 75 80

Glu Asn Ala Val Asp Leu Ser Val Val Val Asn Lys Pro Val Gly Arg
85 90 95

Tyr Arg Ser Ala Pro Lys Arg Leu Ser Met Thr Gln Glu Lys Phe Glu
100 105 110

Met Gly Trp Lys Ala Trp Gly Lys Ser Ile Leu Phe Ala Pro Glu Leu
115 120 125

Ala Asn Ser Thr Phe Val Val Asp Gly Pro Glu Thr Lys Glu Cys Pro
130 135 140

Asp Glu His Arg Ala Trp Asn Ser Met Gln Ile Glu Asp Phe Gly Phe
145 150 155 160

Gly Ile Thr Ser Thr Arg Val Trp Leu Lys Ile Arg Glu Glu Ser Thr
165 170 175

Asp Glu Cys Asp Gly Ala Ile Ile Gly Thr Ala Val Lys Gly His Val
180 185 190

Ala Val His Ser Asp Leu Ser Tyr Trp Ile Glu Ser Arg Tyr Asn Asp
195 200 205

Thr Trp Lys Leu Glu Arg Ala Val Phe Gly Glu Val Lys Ser Cys Thr
210 215 220

Trp Pro Glu Thr His Thr Leu Trp Gly Asp Gly Val Glu Glu Ser Glu
225 230 235 240

Leu Ile Ile Pro His Thr Ile Ala Gly Pro Lys Ser Lys His Asn Arg
245 250 255

Arg Glu Gly Tyr Lys Thr Gln Asn Gln Gly Pro Trp Asp Glu Asn Gly
260 265 270

Ile Val Leu Asp Phe Asp Tyr Cys Pro Gly Thr Lys Val Thr Ile Thr
275 280 285

Glu Asp Cys Gly Lys Arg Gly Pro Ser Val Arg Thr Thr Thr Asp Ser
290 295 300

Gly Lys Leu Ile Thr Asp Trp Cys Cys Arg Ser Cys Ser Leu Pro Pro
305 310 315 320

Leu Arg Phe Arg Thr Glu Asn Gly Cys Trp Tyr Gly Met Glu Ile Arg
325 330 335

Pro Val Arg His Asp Glu Thr Thr Leu Val Arg Ser Gln Val Asp Ala
340 345 350